United States Patent
Janis et al.

(10) Patent No.: US 11,867,706 B2
(45) Date of Patent: Jan. 9, 2024

(54) METHODS AND SYSTEMS TO MEASURE CANNABIDIOL (CBD)

(71) Applicant: Laboratory Corporation of America Holdings, Burlington, NC (US)

(72) Inventors: Gregory C. Janis, Minneapolis, MN (US); Melissa M. Goggin, North Branch, MN (US)

(73) Assignee: Laboratory Corporation of America Holdings, Burlington, NC (US)

( * ) Notice: Subject to any disclaimer, the term of this patent is extended or adjusted under 35 U.S.C. 154(b) by 716 days.

(21) Appl. No.: 16/849,433

(22) Filed: Apr. 15, 2020

(65) Prior Publication Data

US 2020/0326355 A1    Oct. 15, 2020

Related U.S. Application Data

(60) Provisional application No. 62/834,122, filed on Apr. 15, 2019.

(51) Int. Cl.
*G01N 33/94* (2006.01)
*G16B 50/30* (2019.01)
*G16B 50/20* (2019.01)

(52) U.S. Cl.
CPC .......... *G01N 33/948* (2013.01); *G16B 50/20* (2019.02); *G16B 50/30* (2019.02); *G01N 2560/00* (2013.01)

(58) Field of Classification Search
CPC .... G01N 33/948; G01N 33/48; G01N 33/493; G01N 2560/00; G16B 50/20; G16B 50/30
USPC ... 436/63, 93, 131, 161, 173, 174, 175, 177, 436/178, 901; 422/70
See application file for complete search history.

(56) References Cited

U.S. PATENT DOCUMENTS

| | | | |
|---|---|---|---|
| 6,107,623 A | 8/2000 | Bateman et al. | |
| 2009/0159792 A1* | 6/2009 | Day | G01N 33/948 250/282 |
| 2016/0231341 A1* | 8/2016 | Lakshmi Narayanan | G01N 33/9486 |

OTHER PUBLICATIONS

Andersson et al. Analytical & Bioanalytical Chemistry, vol. 408, Jul. 15, 2016, pp. 6461-6471.*
Fletcher et al. Rapid Communcations in Mass Spectrometry, vol. 30, 2016, pp. 908-916.*
Piccolella et al. Journal of Pharmaceutical and Biomedical Analysis, vol. 201, May 5, 2021, 114125: pp. 1-9.*
Goggin et al. Clinical Toxicology, vol. 59, No. 6, 2021, pp. 506-514.*
Anzillotti, L. et al., "Cannabinoids Determination in Oral Fluid By SPME-GC/MS and UHPLC-MS/MS and its Application on Suspected Drivers," Science and Justice, 54(6):421-426 (2014).
Kevin, R. et al., "Urinary Cannabinoid Levels During Nabiximols (Sativex®)-Medicated Inpatient Cannabis Withdrawal," Forensic Toxicology, 35(1):33-44 (2017).
Lee, D. et al., "Can Oral Fluid Cannabinoid Testing Monitor Medication Compliance and/or Cannabis Smoking During Oral THC and Oromucosal Sativex Administration?," Drug and Alcohol Depend., 130(1):68-76 (2013).
Meng, Q. et al., "A Reliable and Validated LC-MS/MS Method for the Simultaneous Quantification of 4 Cannabinoids in 40 Consumer Products," Plos One, 13(5):e0196396 (2018) 16 pages.
CA 3,134,237, Office Action, dated Jul. 12, 2022, 6 pages.
PCT/US2020/028270, International Preliminary Report on Patentability, dated Oct. 28, 2021, 12 pages.
PCT/US2020/028270, International Search Report and Written Opinion, dated Jul. 29, 2020, 13 pages.
Robb, D. et al., "Atmospheric Pressure Photoionization: An Ionization Method for Liquid Chromatography-Mass Spectrometry," Anal. Chem. 72(15): 3653-3659 (2000).
CA 3,134,237, Office Action, dated Feb. 24, 2023, 5 pages.

* cited by examiner

*Primary Examiner* — Maureen Wallenhorst
(74) *Attorney, Agent, or Firm* — Kilpatrick Townsend & Stockton LLP

(57) ABSTRACT

The methods and systems may include LC-MS/MS. For example the method may include obtaining MS/MS data for a predetermined MS/MS transition for THC and/or at least one THC metabolite and CBD and/or at least one CBD metabolite, and determining a ratio of the amount of the CBD and/or at least one CBD metabolite to the amount of the THC and/or at least one THC metabolite for the biological sample. In certain embodiments, the methods and/or systems are used to distinguish CBD from THC use in a subject.

16 Claims, 8 Drawing Sheets

METHODS AND SYSTEMS TO MEASURE CANNABIDIOL (CBD)

RELATED APPLICATIONS

This application claims priority to U.S. provisional patent application No. 62/834,122 filed Apr. 15, 2019. The disclosure of U.S. provisional patent application No. 62/834,122 is incorporated by reference in its entirety herein.

FIELD OF INVENTION

The present disclosure relates to methods and systems to measure cannabidiol (CBD) and in particular, to distinguish CBD from tetrahydrocannabinol (THC) in a subject.

BACKGROUND

Tetrahydrocannabinol (THC) is the primary psychoactive compound present in marijuana; the effects of THC have been known for thousands of years. While debates over medicinal and recreational marijuana and THC continue, a non-psychoactive structural isomer of THC, cannabidiol (CBD), has rapidly emerged as a purported natural remedy for a myriad of ailments. However, true scientific knowledge of the compound's physiology, pharmacology, and metabolism is lacking in all but a few specific instances.

Detecting marijuana use is a component of the tens of millions of urine drug screens which will be performed in the US this year. These tests aid in assessing pre-employment qualifications, workplace safety, medical monitoring, and a variety of questions by targeting the primary urinary metabolite of THC. The sudden meteoric rise of CBD stresses the ability to definitively detect marijuana use. Laboratories must understand the impact of CBD on their testing methodologies to ensure that CBD use cannot falsely appear as marijuana use in a drug test. This is a complex, multifaceted concern. The close structural similarity of CBD to THC results in both compounds following similar metabolic paths, forming parallel isometric metabolites. Methodologies utilized by some drug testing laboratories can be challenged to discriminate the two metabolites by GC or LC techniques. Additionally, some older GC-MS techniques for the analysis of THC inappropriately convert CBD into THC. Even with good analytical techniques, discriminating CBD use from marijuana use remains difficult. Unregulated production of CBD products is frequently contaminated with varying amounts of THC exposing CBD users to coincidental THC. Thus, there is a need for laboratories to be able to differentiate THC and CBD use as well as coincidental exposure to contaminating THC in CBD products from actual marijuana use.

SUMMARY

Disclosed are methods and systems to measure cannabidiol and/or cannabidiol metabolites. In certain embodiments, the methods and systems may be used to distinguish CBD from THC use in a subject. The method may be embodied in a variety of ways.

In one embodiment, disclosed is a method to distinguish CBD use from THC use comprising: measuring CBD and/or at least one CBD metabolite; measuring THC and/or at least one THC metabolite; and comparing the ratio of the CBD and/or at least one CBD metabolite to the THC and/or at least one THC metabolite. In certain embodiments, the method is performed using LC-MS/MS. For example, in certain embodiments, the method may comprise a method to measure relative levels of CBD and/or THC or metabolites of CBD and/or THC in a biological sample comprising the steps of: (a) obtaining MS/MS data comprising a predetermined MS/MS transition for THC and/or at least one THC metabolite and CBD and/or at least one CBD metabolite, wherein the predetermined MS/MS transition comprises a transition for at least one predefined precursor ion of defined m/z and at least one quantitative fragment ion of a defined m/z for each of the THC and/or at least one THC metabolite and the CBD and/or at least one CBD metabolite; (b) determining the amount of the THC and/or at least one THC metabolite and the CBD and/or at least one CBD metabolite in the biological sample based on the transitions in step (a); and (c) determining a ratio of the amount of the CBD and/or at least one CBD metabolite to the amount of the THC and/or at least one THC metabolite for the biological sample.

Also disclosed are systems and computer-program products for performing the disclosed methods.

BRIEF DESCRIPTION OF THE DRAWINGS

The disclosure may be better understood by referring to the following non-limiting drawings.

DETAILED DESCRIPTION

Figure 1:
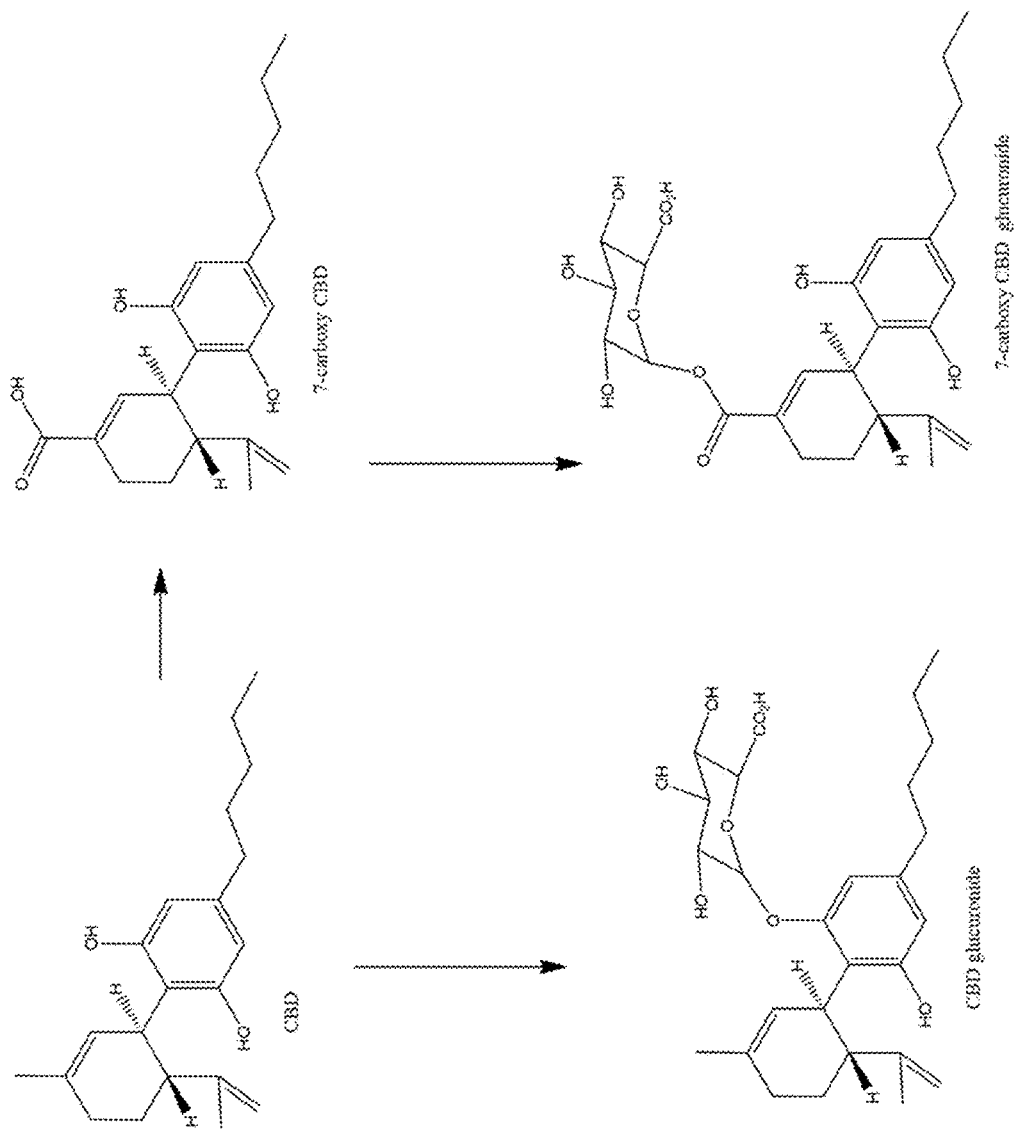
FIG. 1 shows the primary metabolism of CBD.

The presently disclosed subject matter now will be described more fully hereinafter with reference to the accompanying description and drawings, in which some, but not all embodiments of the presently disclosed subject matter are shown. The presently disclosed subject matter can be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims. Although specific terms are employed herein, they are used in a generic and descriptive sense only and not for purposes of limitation.

Definitions

While the following terms are believed to be well understood by one of ordinary skill in the art, the following definitions are set forth to facilitate explanation of the presently disclosed subject matter. Other definitions are found throughout the specification. Unless otherwise defined, all technical and scientific terms used herein have the same meaning as commonly understood by one of ordinary skill in the art to which this presently described subject matter belongs.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10. Additionally, any reference referred to as being "incorporated herein" is to be understood as being incorporated in its entirety.

The terms "a", "an", and "the" refer to "one or more" when used in this application, including the claims. Thus, for example, reference to "a cell" includes a plurality of such cells, unless the context clearly is to the contrary (e.g., a plurality of cells), and so forth.

The term "accuracy" refers to closeness of the agreement between a test result and the accepted reference value expressed as absolute and/or relative bias.

The term "analyte" refers to a compound being measured or detected and/or component represented in the name of a measurable quantity.

The term "analytical measurement range" (AMR) refers to the range of analyte values that a method can directly measure on the specimen without any dilution, concentration, or other pretreatment not part of the usual assay process.

The term "analytic interferences" refers to an artifactual increase or decrease in apparent concentrations, activity, or intensity of an analyte due to the presence of a substance that reacts specifically or nonspecifically with either the detection reagent or the signal itself.

As used herein, a sample may be a "biological sample." The term "biological sample" refers to a sample obtained from a biological source, including, but not limited to, an animal, a cell culture, an organ culture, and the like. Suitable samples include blood, plasma, serum, urine, saliva, tear, cerebrospinal fluid, organ, hair, muscle, or other tissue sample. Or, a sample may not be a biological sample but may be a synthetic (i.e., in vitro) sample, as for example for the analysis of a synthesis product or enzymatic reaction.

The term "specificity" refers to the ability of the measurement procedure to discriminate the analyte of interest when presented with substances potentially found within a sample. In an embodiment, it is expressed as a percent (%) cross-reactivity and/or response to substances other than analyte of interest in the absence of the analyte of interest.

The term "selectivity" refers to the ability of the measurement procedure to accurately measure the analyte of interest without contribution of the substances potentially found within a sample. In an embodiment, it is expressed as a % cross-reactivity and/or response to substances other than analyte of interest in the presence of the analyte of interest.

As used herein, a "subject" may comprise an animal. Thus, in some embodiments, the biological sample is obtained from a mammalian animal, including, but not limited to a dog, a cat, a horse, a rat, a monkey, and the like. In some embodiments, the biological sample is obtained from a human subject. In some embodiments, the subject is a patient, that is, a living person presenting themselves in a clinical setting for diagnosis, prognosis, or treatment of a disease or condition. In some cases, the subject is an employee presenting themselves for drug testing. In some embodiments, the test sample is not a biological sample, but comprises a non-biological sample, e.g., obtained during the manufacture or laboratory analysis of a synthetic analyte, which can be analyzed to determine the composition and/or yield of the manufacturing and/or analysis process.

The terms "purify" or "separate" or derivations thereof do not necessarily refer to the removal of all materials other than the analyte(s) of interest from a sample matrix. Instead, in some embodiments, the terms "purify" or "separate" refer to a procedure that enriches the amount of one or more analytes of interest relative to one or more other components present in the sample matrix. In some embodiments, a "purification" or "separation" procedure can be used to remove one or more components of a sample that could interfere with the detection of the analyte, for example, one or more components that could interfere with detection of an analyte by mass spectrometry.

As used herein, the term "chromatography" refers to a process in which a chemical mixture carried by a liquid or gas is separated into components as a result of differential distribution of the chemical entities as they flow around or over a stationary liquid or solid phase.

The term "Limit of Blank" (LOB) refers to the highest measurement result that is likely to be observed for a blank sample (with a stated probability). LOB is typically expressed as mean plus 1.645×SD (or 2×SD) of blank measurements.

The term "Limit of Detection" (LOD) refers to the lowest amount of analyte in a sample that can be detected (with stated probability). LOD is typically expressed as LOB plus 1.645×SD (or 2×SD) of low sample measurements.

The term "Lower Limit of Quantitation" (LLOQ) refers to the lowest amount of analyte in a sample that can be quantitatively determined with stated acceptable precision and accuracy.

The term "Upper Limit of Quantitation" (ULOQ) refers to the highest amount of analyte in a sample that can be quantitatively determined without dilution.

The term "Intra-run Imprecision" refers to the closeness of the agreement between the results of successive measurements of the same measure and carried under the same conditions of measurements (same analytical run).

The term "Inter-run Imprecision" refers to the closeness of the agreement between independent test results obtained under stipulated conditions (different analytical runs and/or operators, laboratories, instruments, reagent lots, calibrators, etc.).

The term "Maximum Dilution/Concentration" refers to the established laboratory specifications for the maximum dilution and/or concentration that may be performed to obtain a reportable numeric result.

The term "Reference Interval" refers to an interval that, when applied to the population serviced by the laboratory, correctly includes most of the subjects with characteristics similar to the reference group and excludes the others.

As used herein, "liquid chromatography" (LC) refers to a process of selective retardation of one or more components of a fluid solution as the fluid uniformly percolates through a column of a finely divided substance, or through capillary passageways. The retardation results from the distribution of the components of the mixture between one or more stationary phases and the bulk fluid (i.e., mobile phase) as this fluid moves relative to the stationary phase(s). "Liquid chromatography" includes reverse phase liquid chromatography (RPLC), high performance liquid chromatography (HPLC) and high turbulence liquid chromatography (HTLC).

As used herein, the term "HPLC" or "high performance liquid chromatography" refers to liquid chromatography in which the degree of separation is increased by forcing the mobile phase under pressure through a stationary phase, typically a densely packed column. The chromatographic column typically includes a medium (i.e., a packing material) to facilitate separation of chemical moieties (i.e., fractionation). The medium may include minute particles. The particles can include a bonded surface that interacts with the various chemical moieties to facilitate separation of the chemical moieties such as the biomarker analytes quantified in the experiments herein. One suitable bonded surface is a hydrophobic bonded surface such as an alkyl bonded surface. Alkyl bonded surfaces may include C-4, C-8, or C-18 bonded alkyl groups, preferably C-18 bonded groups. The chromatographic column includes an inlet port for receiving a sample and an outlet port for discharging an effluent that includes the fractionated sample. In the method, the sample (or pre-purified sample) may be applied to the column at the inlet port, eluted with a solvent or solvent mixture, and discharged at the outlet port. Different solvent modes may be selected for eluting different analytes of interest. For example, liquid chromatography may be performed using a gradient mode, an isocratic mode, or a polytypic (i.e. mixed) mode.

As used herein, the term "analytical column" refers to a chromatography column having sufficient chromatographic plates to effect a separation of the components of a test sample matrix. Preferably, the components eluted from the analytical column are separated in such a way to allow the presence or amount of an analyte(s) of interest to be determined. In some embodiments, the analytical column comprises particles having an average diameter of about 5 µm. In some embodiments, the analytical column is a functionalized silica or polymer-silica hybrid, or a polymeric particle or monolithic silica stationary phase, such as a phenyl-hexyl functionalized analytical column.

Analytical columns can be distinguished from "extraction columns," which typically are used to separate or extract retained materials from non-retained materials to obtained a "purified" sample for further purification or analysis. In some embodiments, the extraction column is a functionalized silica or polymer-silica hybrid or polymeric particle or monolithic silica stationary phase, such as a Poroshell SBC-18 column.

As used herein, the terms "mass spectrometry" or "MS" generally refer to methods of filtering, detecting, and measuring ions based on their mass-to-charge ratio, or "m/z." In MS techniques, one or more molecules of interest are ionized, and the ions are subsequently introduced into a mass spectrometer where, due to a combination of electric fields, the ions follow a path in space that is dependent upon mass ("m") and charge ("z").

In certain embodiments, the mass spectrometer uses a "quadrupole" system. In a "quadrupole" or "quadrupole ion trap" mass spectrometer, ions in an oscillating radio frequency (RF) field experience a force proportional to the direct current (DC) potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

In certain embodiments, "tandem mass spectrometry" (MS/MS) is used. See, e.g., U.S. Pat. No. 6,107,623, entitled "Methods and Apparatus for Tandem Mass Spectrometry," which is hereby incorporated by reference in its entirety. Tandem mass spectrometry (MS/MS) is the name given to a group of mass spectrometric methods wherein "parent or precursor" ions generated from a sample are fragmented to yield one or more "fragment or product" ions, which are subsequently mass analyzed by a second MS procedure. As used herein, parent and precursor ion are used interchangeably. Also, as used herein fragment and product ions are used interchangeably. MS/MS methods are useful for the analysis of complex mixtures, especially biological samples, in part because the selectivity of MS/MS can minimize the need for extensive sample clean-up prior to analysis. In an example of an MS/MS method, precursor ions are generated from a sample and passed through a first mass filter (quadrupole 1 or Q1) to select those ions having a particular mass-to-charge ratio. These ions are then fragmented, typically by collisions with neutral gas molecules in the second quadrupole (Q2), to yield product (fragment) ions which are selected in the third quadrupole (Q3), the mass spectrum of which is recorded by an electron multiplier detector. The product ion spectra so produced are indicative of the structure of the precursor ion, and the two stages of mass filtering can eliminate ions from interfering species present in the conventional mass spectrum of a complex mixture.

The term "ionization" and "ionizing" as used herein refers to the process of generating an analyte ion having a net electrical charge equal to one or more electron units. Negative ions are those ions having a net negative charge of one or more electron units, while positive ions are those ions having a net positive charge of one or more electron units.

The term "electron ionization" as used herein refers to methods in which an analyte of interest in a gaseous or vapor phase interacts with a flow of electrons. Impact of the electrons with the analyte produces analyte ions, which may then be subjected to a mass spectrometry technique.

The term "chemical ionization" as used herein refers to methods in which a reagent gas (e.g. ammonia) is subjected to electron impact, and analyte ions are formed by the interaction of reagent gas ions and analyte molecules.

The term "field desorption" as used herein refers to methods in which a non-volatile test sample is placed on an ionization surface, and an intense electric field is used to generate analyte ions.

The term "desorption" as used herein refers to the removal of an analyte from a surface and/or the entry of an analyte into a gaseous phase.

The term "matrix-assisted laser desorption ionization," or "MALDI" as used herein refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

The term "surface enhanced laser desorption ionization," or "SELDI" as used herein refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

The term "electrospray ionization," or "ESI," as used herein refers to methods in which a solution is passed along a short length of capillary tube, to the end of which is applied a high positive or negative electric potential. Upon reaching the end of the tube, the solution may be vaporized (nebulized) into a jet or spray of very small droplets of solution in solvent vapor. This mist of droplet can flow through an evaporation chamber which is heated slightly to prevent condensation and to evaporate solvent. As the droplets get smaller the electrical surface charge density increases until such time that the natural repulsion between like charges causes ions as well as neutral molecules to be released.

The term "Atmospheric Pressure Chemical Ionization," or "APCI," as used herein refers to mass spectroscopy methods that are similar to ESI, however, APCI produces ions by ion-molecule reactions that occur within a plasma at atmospheric pressure. The plasma is maintained by an electric discharge between the spray capillary and a counter electrode. Then, ions are typically extracted into a mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "Atmospheric Pressure Photoionization" ("APPI") as used herein refers to the form of mass spectroscopy where the mechanism for the photoionization of molecule M is photon absorption and electron ejection to form the molecular M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+(see e.g., Robb et al., 2000, Anal. Chem. 72(15):3653-3659).

The term "inductively coupled plasma" as used herein refers to methods in which a sample is interacted with a partially ionized gas at a sufficiently high temperature to atomize and ionize most elements.

As used herein, the term "on-line" refers to purification or separation steps that are performed in such a way that the test sample is disposed, e.g., injected, into a system in which the various components of the system are operationally connected and, in some embodiments, in fluid communication with one another.

In contrast to the term "on-line", the term "off-line" refers to a purification, separation, or extraction procedure that is performed separately from previous and/or subsequent purification or separation steps and/or analysis steps. In such off-line procedures, the analytes of interests typically are separated, for example, on an extraction column or by liquid/liquid extraction, from the other components in the sample matrix and then collected for subsequent introduction into another chromatographic or detector system. Off-line procedures typically require manual intervention on the part of the operator.

As used herein, the term multiple reaction monitoring refers to the technique of using tandem mass spectrometry to select and measure more than one parent/precursor and fragment/product pairs within a given analysis.

Methods and Systems to Measure Cannabidiol and Metabolites Thereof

Disclosed are methods and systems to measure cannabinoid metabolites as well as discriminate cannabidiol (CBD) users from marijuana/THC users. The methods and systems may be embodied in a variety of ways.

Donors for urine drug screening or medical monitoring purposes may declare CBD as a medication prior to testing. In some cases, subjects claiming CBD use may be attempting to cover up marijuana and/or THC use to avoid the ramifications of a positive drug test. It can be difficult with currently available analytical techniques for laboratories to discriminate CBD use from marijuana/THC use. Other subjects claiming CBD use are in fact CBD users without any intentional exposure to marijuana or THC.

Figure 2:
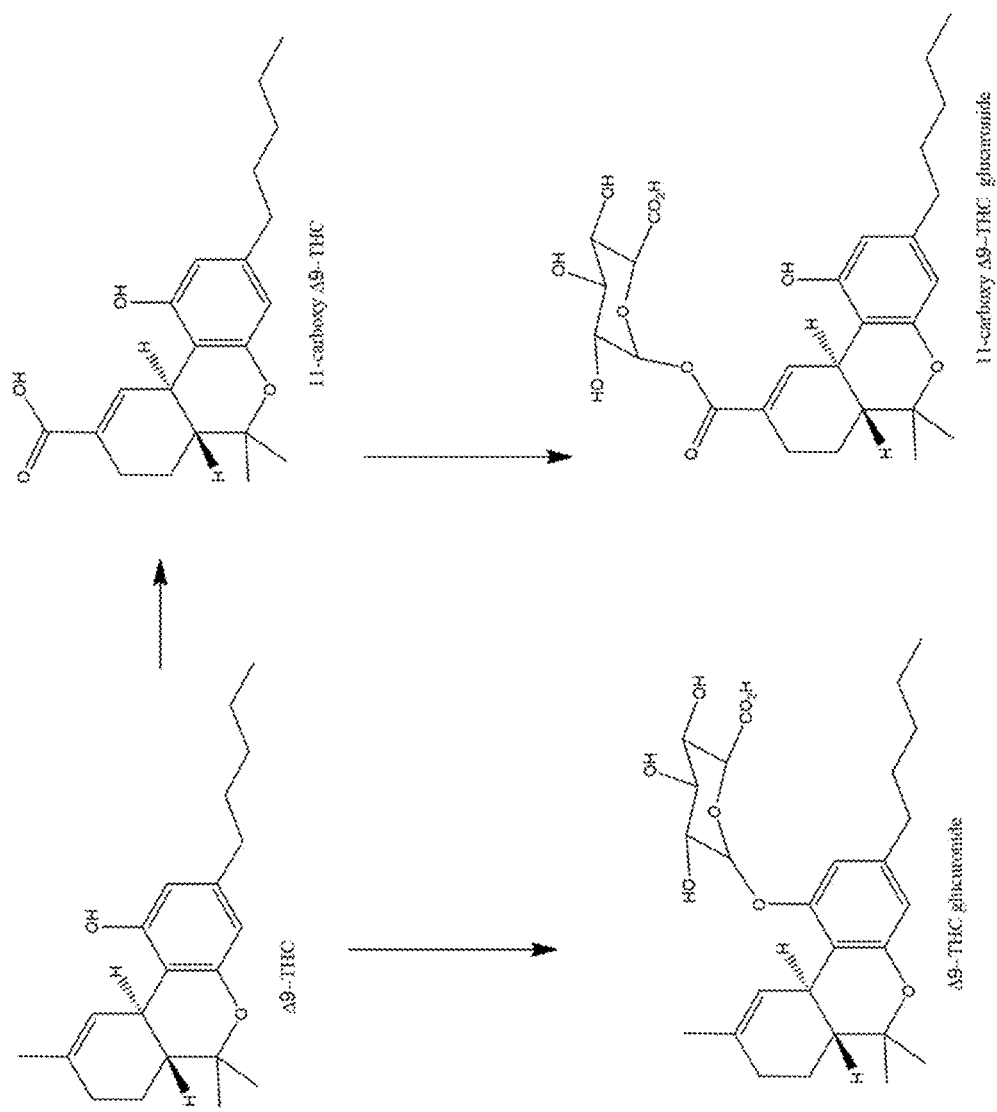
FIG. 2 shows the primary metabolism of THC.

As shown in FIGS. 1 and 2, CBD and THC and their metabolites are structurally very similar to each other thus making identification and discrimination of CBD from THC in samples from subjects challenging. Also, a primary challenge in discriminating CBD users from marijuana users results from a general lack of purity of CBD products—inadvertently exposing CBD users to THC. CBD products are currently unregulated in most circumstances. Thus, most CBD products contain measurable amounts of THC. CBD is harvested from the hemp plant, and the existence of THC in products is often justified by manufacturers using the 2018 Farm Bill which legalized hemp farming as long as the THC content in the hemp is no more than 0.3%. Due to the low THC content in hemp and hemp derived products such as CBD extracts, these products and materials are not considered as psychoactive drugs. Yet the THC content in products can result in urinary THC markers reaching levels which would indicate marijuana use. Adding further confusion, many strains of marijuana and many marijuana products (e.g. edibles and vape solutions) contain CBD in addition to THC.

The disclosed methods and systems can, in certain embodiments, classify samples so as to distinguish positive results as either indicative of CBD or marijuana (THC) use. In certain embodiments, the samples are human urine samples. In an embodiment, THC and/or at least one THC metabolite and CBD and/or at least one CBD metabolite are directly measured, and the metabolic ratios of the CBD and/or CBD metabolite and the THC and/or THC metabolite are compared. In an embodiment, a sample from a marijuana user will have the THC and/or the at least one THC metabolite predominate over CBD and/or the at least one CBD metabolite and/or a user of CBD will have CBD and the at least one CBD metabolite predominate over THC and/or the at least one THC metabolite. Also, in an embodiment a mixed use of CBD and marijuana and/or THC will result in a ratio of metabolites which does not clearly favor one species (i.e., CBD vs THC) over the other.

Methods to Measure Cannabidiol and Metabolites Thereof

In one embodiment, disclosed is a method to distinguish CBD use from THC use in a subject comprising: measuring CBD and/or at least one CBD metabolite in a sample from the subject; measuring THC and/or at least one THC metabolite in the sample; and comparing the ratio of the CBD and/or at least one CBD metabolite to the THC and/or at least one THC metabolite.

In another embodiment, disclosed is a method to measure relative levels of CBD and THC in a biological sample comprising: measuring CBD and/or at least one CBD metabolite; measuring THC and/or at least one THC metabolite; and comparing the ratio of the CBD and/or at least one CBD metabolite to the THC and/or at least one THC metabolite.

The disclosed methods may comprise LC-MS/MS (e.g., HPLC-MS/MS). Thus, in certain embodiments, the measuring of the CBD and/or at least one CBD metabolite and the THC and the at least one THC metabolite is performed by LC-MS/MS. For example, in one embodiment the method may comprise a method to measure relative levels of CBD and/or THC or metabolites of CBD and/or THC in a biological sample comprising the steps of: (a) obtaining MS/MS data comprising a predetermined MS/MS transition for THC and/or at least one THC metabolite and CBD and/or at least one CBD metabolite, wherein the predetermined MS/MS transition comprises a transition for at least one predefined precursor ion of defined m/z and at least one quantitative fragment ion of a defined m/z for each of the THC and/or at least one THC metabolite and the CBD and/or at least one CBD metabolite; (b) determining the amount of the THC and/or at least one THC metabolite and the CBD and/or at least one CBD metabolite in the biological sample based on the transitions in step (a); and (c) determining a ratio of the amount of the CBD and/or at least one CBD metabolite to the amount of the THC and/or at least one THC metabolite for the biological sample. In some embodiments, the method further comprises obtaining MS/MS data comprising a transition for the at least one predefined precursor ion of defined m/z and at least one qualitative fragment ion of a defined m/z for each of the THC and/or at least one THC metabolite and the CBD and/or at least one CBD metabolite. In an embodiment, the transition for at least one precursor ion to at least one qualitative fragment ion is used to confirm the identity of the THC and/or at least one THC metabolite and the CBD and/or at least one CBD metabolite in the sample. In some embodiments, the method may further comprise identifying the biological sample as being from a subject who has ingested THC and/or CBD and/or is indeterminate for ingesting either THC and/or CBD based on the ratio of the amount of CBD and/or at least one CBD metabolite to the amount of THC and/or at least one THC metabolite for the sample.

In various embodiments, the at least one CBD metabolite is 7-carboxy CBD (COO-CBD) as disclosed in FIG. 1. In various embodiments, the at least one THC metabolite is 11-carboxy Δ9-THC (COO-THC) as disclosed in FIG. 2. Also in an embodiment, the CBD comprises CBD released from CBD-glucuronide, and the COO-CBD comprises COO-CBD released from 7-carboxy CBD glucuronide (see FIG. 1). Additionally and/or alternatively, the THC may comprise THC released from Δ9-THC-glucuronide and the COO-THC may comprise COO-THC released from 11-carboxy Δ9-THC glucuronide (see FIG. 2).

In an embodiment, the glucuronide form of the CBD and/or THC is hydrolyzed to release the CBD, THC or their metabolites from the glucuronide moiety prior to the measuring step. Also, in an embodiment, liquid-liquid extraction is used to separate CBD and/or at least one CBD metabolite (e.g., COO-CBD) and or the THC and/or at least one THC metabolite (e.g., COO-THC) from other components in the sample.

In an embodiment, the precursor-product transitions measured by MS/MS are those shown in Table 3. Or other precursor-product transitions may be used. For example, the ionization conditions and/or MS/MS conditions may be varied to allow for the measurement of different precursor-product transitions for each of the CBD and/or CBD metabolite and/or THC and/or THC metabolite analytes.

For example, in an embodiment the predefined precursor ion of defined m/z comprises at least one of: 315.1 m/z for THC; 315.1 m/z for CBD; 345.1 m/z for COO-THC; and/or 345.1 m/z for COO-CBD. Additionally and/or alternatively, the predefined quantitative fragment ion of defined m/z may comprise at least one of: 193.1 m/z for THC; 193.1 m/z for CBD; 193.1 m/z for COO-THC; and/or 193.1 m/z for COO-CBD. Also, in certain embodiments, the predefined qualitative fragment ion of defined m/z may comprise at least one of: 123.1 m/z and/or 259.1 m/z and 135.1 m/z for THC; 123.1 m/z and/or 259.1 m/z and 135.1 m/z for CBD; 299.1 m/z and/or 187.1 m/z and 229.1 m/z for COO-THC; and/or 299.1 m/z and/or 257.1 m/z and 229.1 m/z for COO-CBD.

In various embodiments, a labeled isotope of the CBD and/or at least one CBD metabolite and/or the THC and/or at least one THC metabolite such as those disclosed in Table 3 are used as internal standards. In certain embodiments, the internal standards may comprise at least one of $D_3$-THC, $D_3$-CBD, or $D_9$-COO-THC. Additionally and/or alternatively, in certain embodiments the internal standard $D_9$-COO-THC is used in the measurement of COO-THC and/or COO-CBD. Or, other internal standards may be used (e.g., different isotopes and the like). For example, in certain embodiments, the internal standard may comprise (for MS/MS) at least one of a predefined precursor ion of 318.1 m/z for at least one of $D_3$-THC and $D_3$-CBD and a predefined precursor ion of 354.3 m/z for $D_9$-COO-THC; and/or at least one of a predefined quantitative fragment ion of 196.2 m/z for at least one of $D_3$-THC and $D_3$-CBD and a predefined quantitative fragment ion of 196.1 m/z for $D_9$-COO-THC; and/or at least one of a predefined qualitative fragment ion of 123.1 m/z for at least one of $D_3$-THC and $D_3$-CBD and a predefined qualitative fragment ion of 308.2 m/z for $D_9$-COO-THC.

Additionally and/or alternatively, in certain embodiments the THC and/or at least one THC metabolite and the CBD and/or at least one CBD metabolite exhibit different multiple reaction monitoring retention times as illustrated in the Examples herein.

The method may distinguish CBD use from marijuana use. In an embodiment, a ratio of 2, 3, 4, 5, 6, 7, 8, 9, 10, 15, 20 or greater for the CBD and/or at least one CBD metabolite as compared to the THC and/or at least one THC metabolite indicates CBD use. Additionally and/or alternatively, a ratio of less than 0.2, 0.3, 0.4, 0.5, 0.6, 0.7, 0.8, 0.9 or 1.0 for the CBD and/or at least one CBD metabolite as compared to the THC and/or at least one THC metabolite indicates THC use. In one embodiment, a ratio of greater than 10 for the CBD and/or at least one CBD metabolite as compared to the THC and/or at least one THC metabolite indicates CBD use and/or a ratio of less than 1.0 for the CBD and/or at least one CBD metabolite as compared to the THC and/or at least one THC metabolite indicates THC use.

A variety of biological samples may be used with the disclosed method. In an embodiment, the sample is urine.

The method may comprise a computerized analysis of the results. For example, in an embodiment at least some of the steps are computer-implemented and/or performed using a computer and computer-program product as described herein.

Figure 3:
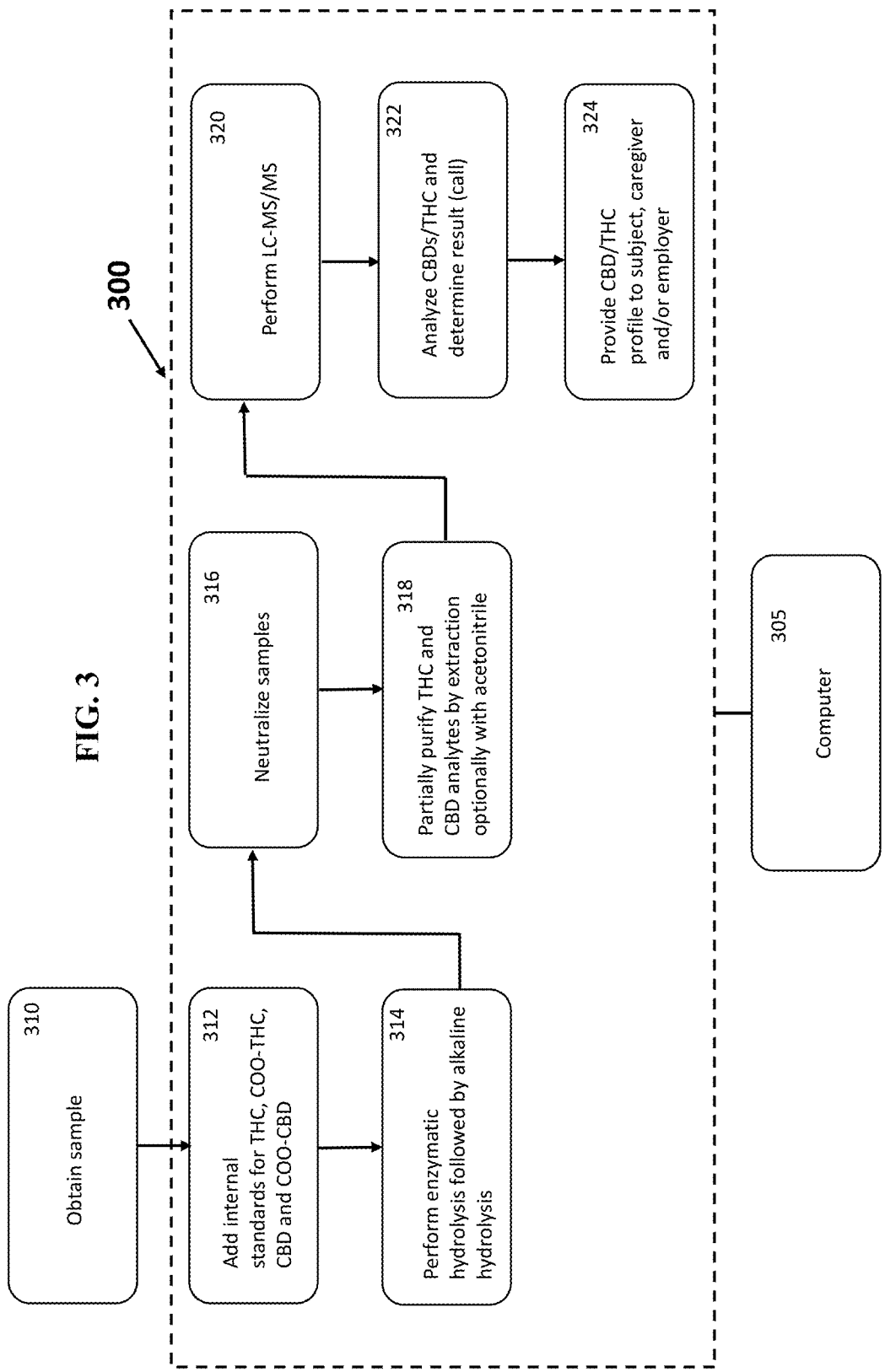
FIG. 3 shows a method for distinguishing CBD and CBD metabolites from THC and THC metabolites in accordance with an embodiment of the disclosure.

FIG. 3 shows an illustration of an embodiment of the disclosed method. Thus, as shown in FIG. 3, the method may include the step 310 of obtaining a biological sample (e.g., urine) from a client interested in determining whether a subject has been using THC or CBD (e.g., drug testing). The sample may then be processed at a single facility or some of the steps may be performed at distinct locations. In some cases internal standards for THC and metabolites of THC and/or CBD and/or metabolites of CBD are added (312). Such standards are described in more detail herein and can provide the ability to correct for quantitative losses and/or inefficiencies that may occur at any step. At this point, the sample may be subjected to enzymatic hydrolysis followed by alkaline hydrolysis (314) to release CBD and its metabolites (e.g., COO-CBD) and THC and its metabolites (e.g., COO-THC) from their glucuronide forms. The samples are then neutralized (e.g., by the addition of HCL in buffer) (316). Next, the samples may be subjected to organic extraction (318) to separate the CBD and its metabolites and the THC and its metabolites from other constituents (e.g., proteins and salts) in the sample.

At this point the samples are ready for LC-MS/MS (320). In some cases the LC is UPLC and the MS/MS is ESI tandem mass spectrometry as described in the Examples herein. The LC-MS/MS results may then be analyzed as disclosed in detail herein and the ratio of CBD and CBD metabolites to THC and THC metabolites is determined (322). The results may then be provided to the subject or their employer or caregiver upon request. Also, in some embodiments the LC-MS/MS and/or the analysis system (or any other step) may be computer-implemented (i.e., linked to a data processor and/or computer) (305) as discussed in more detail herein.

Systems to Measure CBD

In other embodiments, disclosed is a system and/or a computer-program product for performing the methods disclosed herein for determining the presence or amount of CBD and/or one or more CBD metabolites in a sample and/or to distinguish the use of CBD vs. THC by a subject from which the sample has been obtained. Each of the embodiments disclosed herein may be applied to the disclosed systems and/or computer-program products.

For example, in some embodiments the system may comprise: a station for providing a sample believed to contain at least one CBD and/or one or more CBD metabolite; a station for chromatographically separating the at least one CBD and/or one or more CBD metabolite from other components in the sample; and a station for analyzing the chromatographically separated at least one CBD and/or one or more CBD metabolite by mass spectrometry to determine the presence or amount of the one or more biomarkers in the sample. In certain embodiment, the system may comprise one or more computers, and a non-transitory computer readable storage medium containing instructions which, when executed on the one or more computers, cause the one or more computers to perform actions at any of the stations.

Thus, in certain embodiments, the system may comprise a system to measure relative levels of CBD and/or THC or metabolites of CBD and/or THC in a biological sample comprising: one or more computers; and a non-transitory computer readable storage medium containing instructions which, when executed on the one or more computers, cause the one or more computers to perform actions comprising at least one of the following steps: (a) measuring CBD and/or at least one CBD metabolite; (b) measuring THC and/or at least one THC metabolite; and (c) determining a ratio of the amount of the CBD and/or at least one CBD metabolite to the amount of the THC and/or at least one THC metabolite for the sample.

Also, the computer-program product may comprise a computer-program product tangibly embodied in a non-transitory machine-readable storage medium, including instructions configured to run the systems and/or perform the methods of any of the disclosed embodiments. Thus, the computer-program product may comprise a computer-program product tangibly embodied in a non-transitory machine-readable storage medium, including instructions configured to cause one or more computers to perform actions including: (a) measuring CBD and/or at least one CBD metabolite; (b) measuring THC and/or at least one THC metabolite; and (c) determining a ratio of the amount of the CBD and/or at least one CBD metabolite to the amount of the THC and/or at least one THC metabolite for the sample.

As disclosed herein, in certain embodiments, the measuring of the CBD and/or at least one CBD metabolite and the THC and the at least one THC metabolite is performed by LC-MS/MS.

Thus, in some embodiments, disclosed is a system to measure relative levels of CBD and/or THC or metabolites of CBD and/or THC in a biological sample comprising: (a) a station for obtaining MS/MS data comprising a predetermined MS/MS transition for THC and/or at least one THC metabolite and CBD and/or at least one CBD metabolite, wherein the predetermined MS/MS transition comprises a transition for at least one predefined precursor ion of defined m/z and at least one quantitative fragment ion of a defined m/z for each of the THC and/or at least one THC metabolite and the CBD and/or at least one CBD metabolite; (b) a station for determining the amount of the THC and/or at least one THC metabolite and the CBD and/or at least one CBD metabolite in the biological sample based on the transitions in step (a); and (c) a station for determining a ratio of the amount of the CBD and/or at least one CBD metabolite to the amount of the THC and/or at least one THC metabolite for the biological sample. In an embodiment, the station for obtaining MS/MS data further comprises determining a transition for the at least one predefined precursor ion of defined m/z and at least one qualitative fragment ion of a defined m/z for each of the THC and/or at least one THC metabolite and the CBD and/or at least one CBD metabolite. In an embodiment, the transition for at least one precursor ion to at least one qualitative fragment ion is used to confirm the identity of the THC and/or at least one THC metabolite and the CBD and/or at least one CBD metabolite in the sample. In an embodiment, at least one station comprises one or more computers and a non-transitory computer readable storage medium containing instructions which, when executed on the one or more computers, cause the one or more computers to perform an action for the at least one station.

Also disclosed is a computer-program product tangibly embodied in a non-transitory machine-readable storage medium, including instructions configured to cause one or more computers to perform actions to measure relative levels of CBD and/or THC or metabolites of CBD and/or THC in a biological sample comprising at least one of the following steps: (a) obtaining MS/MS data comprising a predetermined MS/MS transition for THC and/or at least one THC metabolite and CBD and/or at least one CBD metabolite, wherein the predetermined MS/MS transition comprises a transition for at least one predefined precursor ion of defined m/z and at least one quantitative fragment ion of a defined m/z for each of the THC and/or at least one THC metabolite and the CBD and/or at least one CBD metabolite; (b) determining the amount of the THC and/or at least one THC metabolite and the CBD and/or at least one CBD metabolite in the biological sample based on the transitions in step (a); and (c) determining a ratio of the amount of the CBD and/or at least one CBD metabolite to the amount of the THC and/or at least one THC metabolite for the biological sample. In an embodiment, the obtaining MS/MS data further comprises determining a transition for the at least one predefined precursor ion of defined m/z and at least one qualitative fragment ion of a defined m/z for each of the THC and/or at least one THC metabolite and the CBD and/or at least one CBD metabolite. In an embodiment, the transition for at least one precursor ion to at least one qualitative fragment ion is used to confirm the identity of the THC and/or at least one THC metabolite and the CBD and/or at least one CBD metabolite in the sample.

In some embodiments, the system and/or computer-program product may further comprise a station and/or instructions, respectively, for identifying the biological sample as being from a subject who has ingested THC and/or CBD and/or is indeterminate for ingesting either THC and/or CBD based on the ratio of the amount of CBD and/or at least one CBD metabolite to the amount of THC and/or at least one THC metabolite for the sample.

In various embodiments of the systems and computer-program products, the at least one CBD metabolite is 7-carboxy CBD (COO-CBD) as disclosed in FIG. 1. In various embodiments, the at least one THC metabolite is 11-carboxy Δ9-THC (COO-THC) as disclosed in FIG. 2. Also in an embodiment, the CBD comprises CBD released from CBD-glucuronide, and the COO-CBD comprises COO-CBD released from 7-carboxy CBD glucuronide (see FIG. 1). Additionally and/or alternatively, the THC may comprise THC released from Δ9-THC-glucuronide and the COO-THC may comprise COO-THC released from 11-carboxy Δ9-THC glucuronide (see FIG. 2).

In various embodiments of the systems and computer-program products, the system may comprise a station (or computer-implemented instructions) for treating the sample such that glucuronide form of the CBD and/or at least one CBD metabolite and/or THC and/or at least one THC metabolite is hydrolyzed to free the CBD, THC and/or their metabolites from the glucuronide prior to the measuring step. Also, in an embodiment of the systems and computer-program products, the system may comprise a station (and/or computer-implemented instructions) for liquid-liquid extraction to separate CBD and/or at least one CBD metabolite (e.g., COO-CBD) and or the THC and/or at least one THC metabolite (e.g., COO-THC) from other components in the sample.)

In various embodiments of the systems and computer-program products, the precursor-product transitions measured by MS/MS are those shown in Table 3. Or other precursor-product transitions may be used. For example, the ionization conditions and/or MS/MS conditions may be varied to allow for the measurement of different precursor-product transitions for each of the CBD and/or CBD metabolite and/or THC and/or THC metabolite analytes.

For example, in an embodiment, the predefined precursor ion of defined m/z comprises at least one of: 315.1 m/z for THC; 315.1 m/z for CBD; 345.1 m/z for COO-THC; and/or 345.1 m/z for COO-CBD. Additionally and/or alternatively, the predefined quantitative fragment ion of defined m/z may comprise at least one of: 193.1 m/z for THC; 193.1 m/z for CBD; 193.1 m/z for COO-THC; and/or 193.1 m/z for COO-CBD. Also, in certain embodiments, the predefined qualitative fragment ion of defined m/z may comprise at least one of: 123.1 m/z and/or 259.1 m/z and 135.1 m/z for THC; 123.1 m/z and/or 259.1 m/z and 135.1 m/z for CBD; 299.1 m/z and/or 187.1 m/z and 229.1 m/z for COO-THC; and/or 299.1 m/z and/or 257.1 m/z and 229.1 m/z for COO-CBD.

In various embodiments of the systems and computer-program products, there is a station (or computer-program product instructions) for addition of labeled isotopes of the CBD and/or at least one CBD metabolite and/or the THC and/or at least one THC metabolite such as those disclosed in Table 3 as internal standards. In certain embodiments, the internal standards may comprise at least one of $D_3$-THC, $D_3$-CBD, or $D_9$-COO-THC. Additionally and/or alternatively, in certain embodiments the internal standard $D_9$-COO-THC is used in the measurement of COO-THC and/or COO-CBD. Or, other internal standards may be used (e.g., different isotopes and the like). For example, in certain embodiments, the internal standard may comprise (in MS/MS) at least one of a predefined precursor ion of 318.1 m/z for at least one of $D_3$-THC and $D_3$-CBD and a predefined precursor ion of 354.3 m/z for $D_9$-COO-THC; and/or at least one of a predefined quantitative fragment ion of 196.2 m/z for at least one of $D_3$-THC and $D_3$-CBD and a predefined quantitative fragment ion of 196.1 m/z for $D_9$-COO-THC; and/or at least one of a predefined qualitative fragment ion of 123.1 m/z for at least one of $D_3$-THC and $D_3$-CBD and a predefined qualitative fragment ion of 308.2 m/z for $D_9$-COO-THC.

Figure 6:
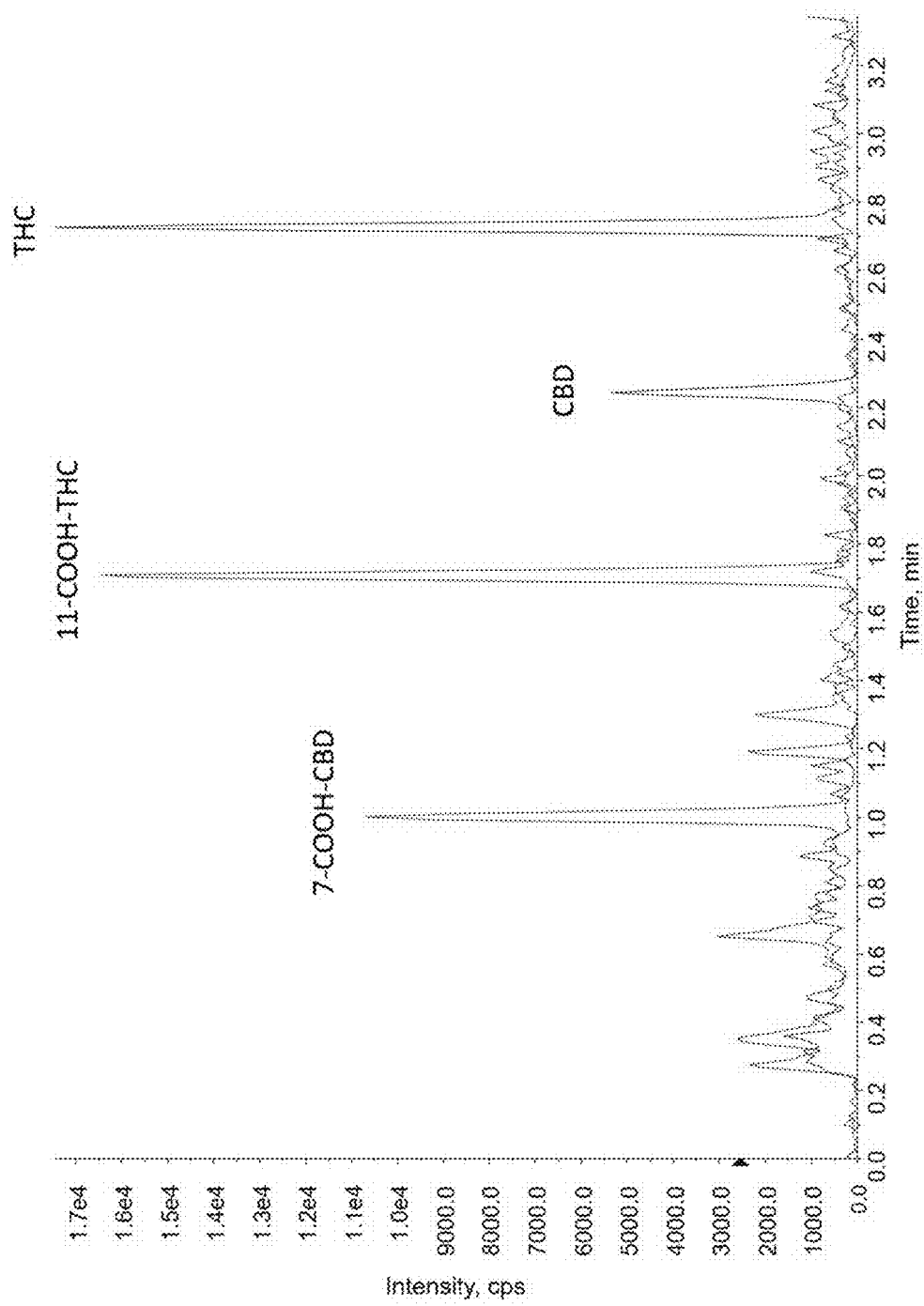
FIG. 6 shows a chromatographic overlay of THC, CBD, COO-THC, and COO-CBD in accordance with an embodiment of the disclosure.

Additionally and/or alternatively, in certain embodiments the THC and/or at least one THC metabolite and the CBD and/or at least one CBD metabolite exhibit different multiple reaction monitoring retention times as illustrated in the Examples herein (e.g., FIG. 6).

The method may distinguish CBD use from marijuana use. In an embodiment, a ratio of 2, 3, 4, 5, 6, 7, 8, 9, 10, 15, 20 or greater for the CBD and/or at least one CBD metabolite as compared to the THC and/or at least one THC metabolite indicates CBD use. Additionally and/or alternatively, a ratio of less than 0.2, 0.3, 0.4, 0.5, 0.6, 0.7, 0.8, 0.9 or 1.0 for the CBD and/or at least one CBD metabolite as compared to the THC and/or at least one THC metabolite indicates THC use. In one embodiment, a ratio of greater than 10 for the CBD and/or at least one CBD metabolite as compared to the THC and/or at least one THC metabolite indicates CBD use and/or a ratio of less than 1.0 for the CBD and/or at least one CBD metabolite as compared to the THC and/or at least one THC metabolite indicates THC use.

Figure 4:
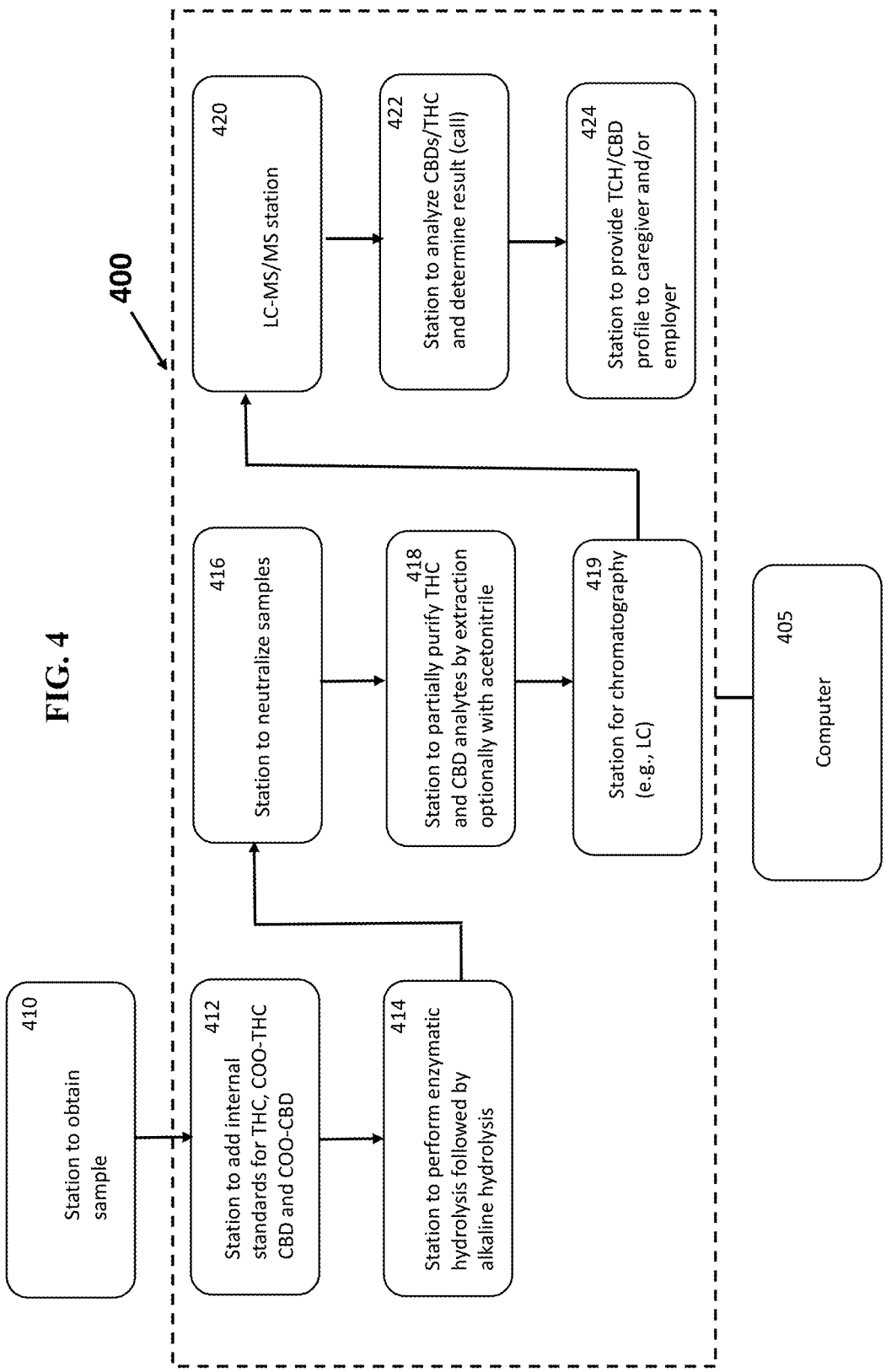
FIG. 4 shows a system for distinguishing CBD and CBD metabolites from THC and THC metabolites in accordance with an embodiment of the disclosure.

A variety of biological samples may be used with the disclosed method. In an embodiment, the sample is urine. FIG. 4 shows a system 400 of the disclosure. It will be understood that in some embodiments, certain steps may not require separate stations, but can be performed at the same station. Thus, as shown in FIG. 4, the system may include a station (410) to perform the step of obtaining a biological sample (e.g., urine) from a client interested in determining whether a subject has been using THC or CBD (e.g., drug testing). The system may also include a station for adding internal standards for THC and metabolites of THC and/or CBD and/or metabolites of CBD (412). Such standards are described in more detail herein and can provide the ability to correct for quantitative losses and/or inefficiencies that may occur at any step. The system may also include a station to subject the sample to enzymatic hydrolysis followed by alkaline hydrolysis (414) to release CBD and its metabolites (e.g., COO-CBD) and THC and its metabolites (e.g., COO-THC) from their glucuronide forms. The system may also include a station for neutralizing the sample (e.g., by the addition of HCL in buffer) (416). In an embodiment, the station for hydrolysis and neutralization may be the same. The system may also include a station for subjecting the sample to partial purification by organic extraction (418) to separate the CBD and its metabolites and the THC and its metabolites from other constituents (e.g., proteins) in the sample. In an embodiment, the station for partial purification (e.g., liquid-liquid extraction) may comprise equipment and reagents for addition of solvents to the sample and removal of waste fractions. Thus, the station for liquid-liquid extraction may comprise a hood or other safety features required for working with solvents At this point the samples may be transferred to the station for chromatographic separation (419) followed by MS/MS (420). In one embodiment, the station for chromatographic separation comprises at least one apparatus to perform liquid chromatography (LC). In one embodiment, the station for liquid chromatography comprises HPLC as disclosed herein. Or, other types of HPLC may be used. In an embodiment, the mass spectrometry is tandem mass spectrometry (MS/MS). In an embodiment, the mass spectrometry is operated in an ESI mode as disclosed herein. Or, other ionization techniques, can be used. In some cases the LC is UPLC and the MS/MS is ESI tandem mass spectrometry as described in the Examples herein.

The system may also include a station for analysis of the data (422). The LC-MS/MS results may then be analyzed as disclosed in detail herein and the ratio of CBD and CBD metabolites to THC and THC metabolites is determined. The results may then be provided (424) to the subject or their employer or caregiver upon request.

In some embodiments, some or all of the stations may be linked to a computer (405) as discussed in more detail herein. For example, in certain embodiments, at least some of the steps are automated such that little to no manual intervention is required.

In some embodiments, one or more of the purification or separation steps can be performed "on-line." The on-line system may comprise an autosampler for removing aliquots of the sample from one container and transferring such aliquots into another container. For example, an autosampler may be used to transfer the sample after extraction onto an LC extraction column. The on-line system may comprise one or more injection ports for injecting the fractions isolated from the LC extraction columns onto the LC analytical column and/or one or more injection ports for injecting the LC purified sample into the MS system. Thus, the on-line system may comprise one or more columns, including but not limited to, an HPLC column. In such "on-line" systems, the test sample and/or analytes of interest can be passed from one component of the system to another without exiting the system, e.g., without having to be collected and then disposed into another component of the system.

In some embodiments, the on-line purification or separation method is highly automated. In such embodiments, the steps can be performed without the need for operator intervention once the process is set-up and initiated. For example, in one embodiment, the system, or portions of the system may be controlled by a computer or computers. Thus, in certain embodiments, the system may comprise software for controlling the various components of the system, including pumps, valves, autosamplers, and the like. Such software can be used to optimize the extraction process through the precise timing of sample and solute additions and flow rate.

Although some or all of the steps in the method and the stations comprising the system may be on-line, in certain embodiments, some or all of the steps may be performed "off-line."

The systems and computer products may perform any of the methods disclosed herein. One or more embodiments described herein can be implemented using programmatic modules, engines, or components. A programmatic module, engine, or component can include a program, a sub-routine, a portion of a program, or a software component or a hardware component capable of performing one or more stated tasks or functions. As used herein, a module or component can exist on a hardware component independently of other modules or components. Alternatively, a module or component can be a shared element or process of other modules, programs or machines.

Figure 5:
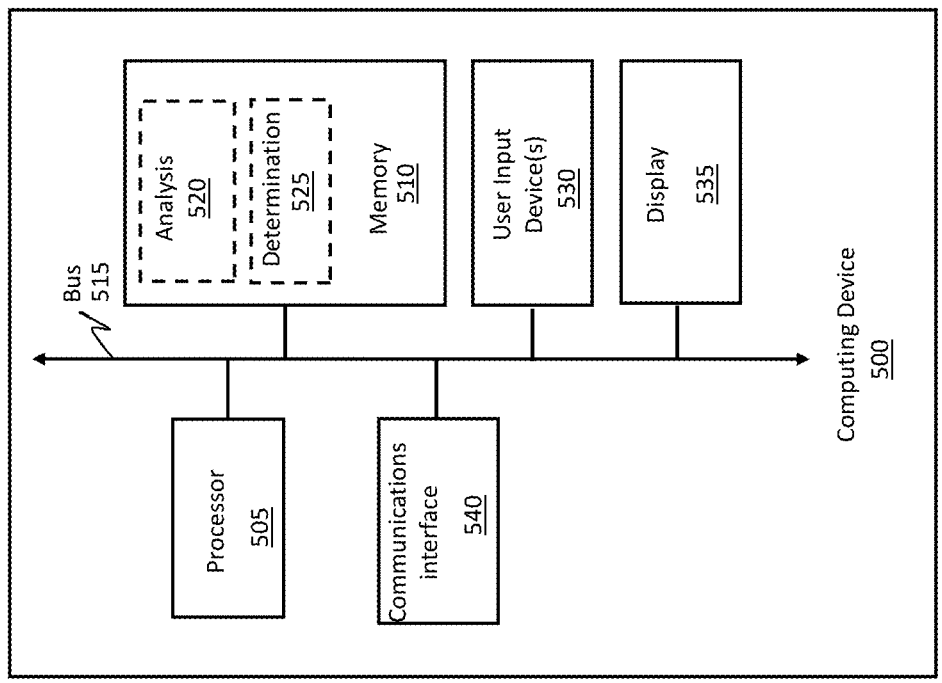
FIG. 5 shows a computer-implemented analysis system for distinguishing CBD and CBD metabolites from THC and THC metabolites in accordance with an embodiment of the disclosure.

FIG. 5 shows a block diagram of a CBD/THC analysis system. As illustrated in FIG. 5, modules, engines, or components (e.g., program, code, or instructions) executable by one or more processors that may be used to implement the various subsystems of an analyzer system according to various embodiments. The modules, engines, or components may be stored on a non-transitory computer medium. As needed, one or more of the modules, engines, or components may be loaded into system memory (e.g., RAM) and executed by one or more processors of the analyzer system. In the example depicted in FIG. 5, modules, engines, or components are shown for implementing the methods and/or systems of the disclosure.

Thus, FIG. 5 illustrates an example computing device 500 suitable for use with systems and the methods according to this disclosure. The example computing device 500 includes a processor 505 which is in communication with the memory 510 and other components of the computing device 500 using one or more communications buses 515. The processor 505 is configured to execute processor-executable instructions stored in the memory 510 to perform one or more methods for assessing CBD and THC levels according to different examples, such as part or all of the example processes 300 or systems 400 described above with respect to FIGS. 3 and 4. In this example, the memory 510 stores processor-executable instructions that provide CBD/THC analysis 520, as discussed herein.

The computing device 500 in this example also includes one or more user input devices 530, such as a keyboard, mouse, touchscreen, microphone, etc., to accept user input. The computing device 500 also includes a display 535 to provide visual output to a user such as a user interface. The computing device 500 also includes a communications interface 540. In some examples, the communications interface 540 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

Embodiments may provide certain advantages. In certain embodiments, the methods and systems may provide greater sensitivity and/or specificity than the sensitivities previously attainable for many of the analytes being measured. Advantages further include the ability to distinguish THC use from CBD use in a subject.

As another advantage, the specificity and sensitivity provided by the disclosed methods and systems may allow for the analysis of analytes from a variety of biological materials. For example, the disclosed methods can be applied to the quantification of analytes of interest in complex sample biological matrices, including, but not limited to, urine, blood, serum, plasma, saliva, and the like. Also, using the disclosed methods and systems allows for measurement of CBDs without derivatization and at levels as low as 60 ng/dL. Thus, the methods and systems are suitable for clinical applications and/or clinical trials.

As additional potential advantages, in certain embodiments, the disclosed systems and methods provide approaches for addressing isobaric interferences, varied sample content, including hemolysed and lipemic samples, while attaining low ng/dL limits of quantification (LLOQ) of the target analytes. Accordingly, embodiments of the disclosed methods and systems may provide for the quantitative, sensitive, and specific detection of clinical biomarkers used in clinical diagnosis.

EXAMPLES

Example 1—Analytical Method

The procedure validated herein is designed to simultaneously detect and quantify metabolites of the cannabinoids THC and CBD. Quantitative analysis utilizes a concurrently processed and analyzed six-point calibration curve with matched stable-label isotopes as internal standards (except for COO-CBD). The targeted analytes are analyzed over the concentration ranges listed below in Table 1.

The intended goal of the assay is two-fold. The assay allows the discrete monitoring of two markers of THC exposure and two markers of CBD exposure. As such, the assay can be utilized to monitor compliance to physician recommended CBD regiments. Furthermore, from an evaluation of the individual metabolic profiles, the assay has a stated goal of being capable of distinguishing a CBD user from a marijuana or THC user.

TABLE 1

| Analytical Measurement Range | |
|---|---|
| Analyte[1] | AMR (ng/mL) |
| THC | 0.60-300.00 |
| COO-THC | 3.00-1500.00 |
| CBD | 0.60-300.00 |
| COO-CBD | 3.00-1500.00 |

[1]All analytes are the free compounds released from their respective phase II metabolic conjugates.

Briefly, 0.100 mL of human urine was mixed with 20.0 µL of a mixture of $D_3$-THC, $D_3$-CBD, and $D_9$-COO-THC as internal standards. Phase II glucuronide conjugates of each of the analytes are released using a two-part hydrolysis procedure. Enzymatic hydrolysis occurs first. To sample aliquots the following reagents were added: 100 µL of 1M acetate hydrolysis buffer pH 5.0, and 25 µL O-glucuronidase from red abalone. Enzymatic hydrolysis was performed for 1 hour at 55° C. An alkaline hydrolysis was performed following the enzymatic hydrolysis. The incubated samples were allowed to reach room temperature and then 20 µL of 12M potassium hydroxide was added and the mixture was allowed to incubate for 5 minutes. Following incubation, the samples were neutralized by the addition of 50 µL of 5M ammonium acetate buffer and 30 µL of 6M HCl.

Acetonitrile partitioning was then performed to isolate the analytes from the aqueous matrix solution. 400 µL of acetonitrile was added and the solution mixed by vortexing. The mixture was then centrifuged to separate the aqueous and organic layers. 200 µL of the acetonitrile layer was transferred to a new 1 mL 96-well plate, or vials with inserts.

The supernatant was then analyzed via UPLC ESI+MS/MS. Chromatography was performed using a gradient elution initially comprised of 55% 10 mM ammonium acetate with 0.1% formic acid and 45% acetonitrile at a flow rate of 650 µL/min through an Acquity UPLC HSS T3 column (50×2.1 mm, 1.8 µm). The full gradient program is detailed in Table 2. Chromatographic system components and parameters are detailed in Table 4.

Targeted cannabinoids were quantified by monitoring the transitions as listed in Table 3. A composite chromatogram is presented in FIG. 6. Quantitation is performed using analyte to internal standard area ratios and $1/x^2$ weighted linear calibration curves.

As validated, the analytical instrumentation consisted of Waters Acquity UPLC connected to a Sciex API 6500+ tandem mass spectrometer.

TABLE 2

| UPLC Gradient Method | | | |
|---|---|---|---|
| Time (minute) | A % | B % | Flow (mL/min) |
| 0.00 | 55 | 45 | 0.650 |
| 0.20 | 55 | 45 | 0.650 |
| 0.30 | 45 | 55 | 0.650 |
| 0.80 | 44 | 56 | 0.650 |
| 1.60 | 30 | 70 | 0.650 |
| 2.00 | 28 | 72 | 0.650 |
| 2.40 | 15 | 85 | 0.650 |
| 2.80 | 15 | 85 | 0.650 |
| 3.00 | 10 | 90 | 0.650 |
| 3.10 | 5 | 95 | 0.650 |
| 3.30 | 5 | 95 | 0.650 |
| 3.35 | 55 | 45 | 0.650 |

TABLE 3

Monitored Tandem Mass Spectrometer Transitions

| Analyte | Precursor [1] (m/z) | Quantitative Fragment Mass (m/z) | Qualitative Fragment 1 Mass (m/z) | Qualitative Fragment 2 Mass (m/z) | Retention Time | Internal Standard Used |
|---|---|---|---|---|---|---|
| THC | 315.1 | 193.1 | 123.1 | 259.1 + 135.1 | 2.73 | $D_3$-THC |
| CBD | 315.1 | 193.1 | 123.1 | 259.1 + 135.1 | 2.25 | $D_3$-CBD |
| COO-THC | 345.1 | 193.1 | 299.1 | 187.1 + 229.1 | 1.71 | $D_9$-COO-THC |
| COO-CBD | 345.1 | 193.1 | 299.1 | 257.1 + 229.1 | 1.01 | $D_9$-COO-THC |
| $D_3$-THC | 318.1 | 196.2 | 123.1 | — | 2.73 | — |
| $D_3$-CBD | 318.1 | 196.2 | 123.1 | — | 2.25 | — |
| $D_9$-COO-THC | 354.3 | 196.1 | 308.2 | — | 1.69 | — |

[1] The precursor ion for all analytes in the methodology consists of the M + 1 pseudomolecular ion.

TABLE 4

Chromatographic Equipment and Parameters

| Parameter | Value |
|---|---|
| Column Type and Manufacturer: | Waters HSS T3 |
| Column Particle Size: | 1.8 μm |
| Column Dimensions: | 50 × 2.1 mm |
| Guard Column and Manufacturer: | Thermo Scientific C18 Javelin |
| Guard Column Particle Size: | 5 μm |
| Guard Column Dimensions: | 10 × 2.1 mm |
| Column Temperature: | 50° C. |
| Mobile Phase A: | 10 mM Ammonium Acetate with 0.1% Formic Acid |
| Mobile Phase B: | Acetonitrile |
| Mobile Phase % A (initial): | 55.0% |
| Mobile Phase % B (initial): | 45.0% |
| Flow Rate: | 650 μL/min |
| Injection Volume: | 3 μL [1] |
| Autosampler Temperature: | 10° C. |

[1] Injection volume utilized during the validation; injection volume may be adjusted during production to maintain linearity.

Example 2—Results

Samples from pain management patients claiming CBD use were analyzed using the methodology described. An example of a chromatographic overlay of CBD, 7-COO-CBD, THC and 11-COO-THC is shown in FIG. 6. A sampling of results is displayed in FIG. 7. Visual analysis of the metabolic ratios clearly indicates a group where CBD use is extremely unlikely due to a lack of CBD metabolites or trace levels of CBD metabolites (left). These donors are clearly marijuana users. A second clustering of metabolic profiles are highly likely to be indicative of CBD use with little or no THC exposure (center). A third group visually appears difficult to interpret the metabolic ratios (right).

Figure 7:
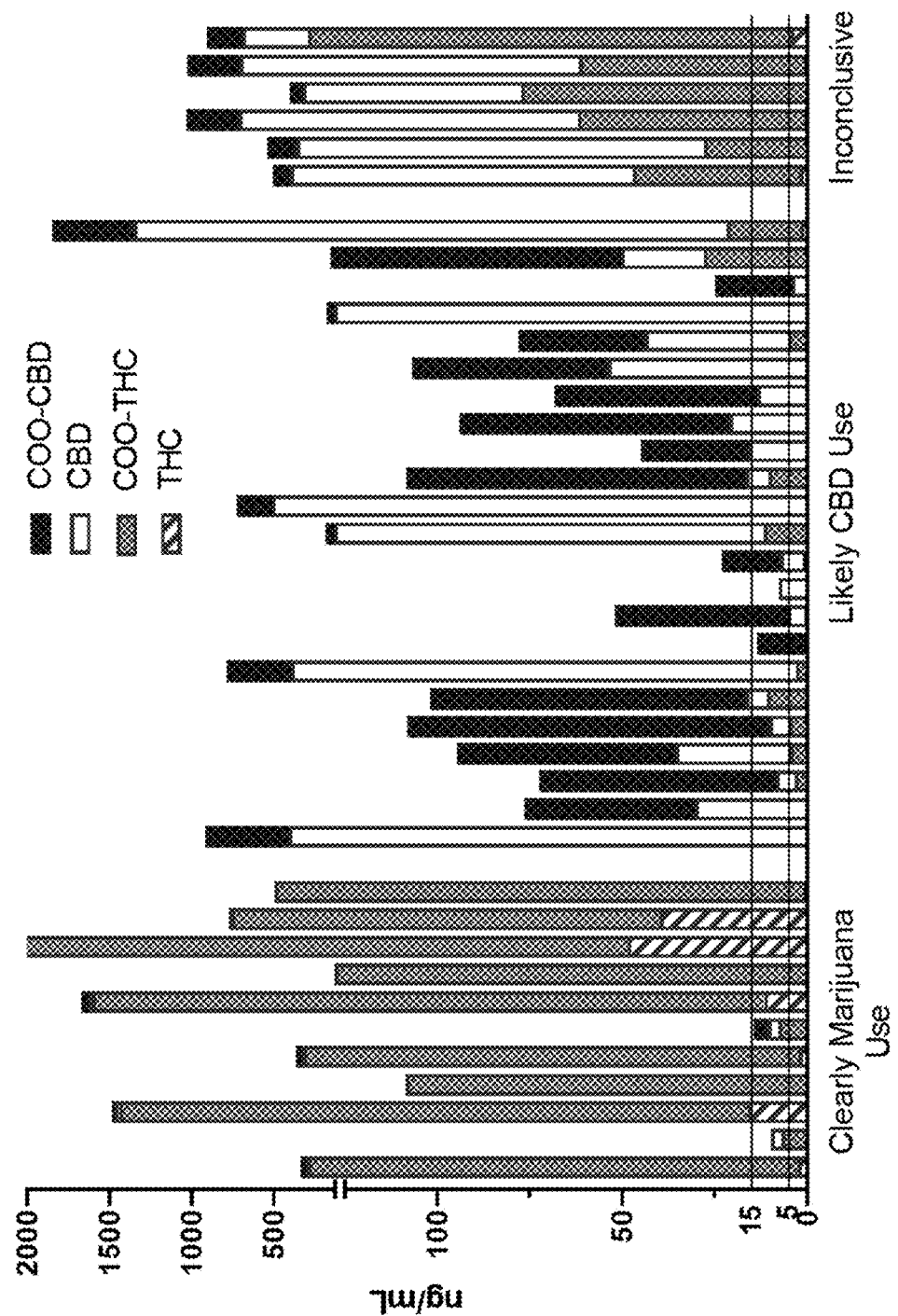
FIG. 7 shows metabolic profiles from individuals claiming CBD use in accordance with an embodiment of the disclosure.

The data presented in FIG. 7 was mathematically converted into a ratio of the sum of the measured CBD metabolites (unconjugated CBD and unconjugated COO-CBD) over the sum of the measured metabolites (unconjugated THC and unconjugated COO-THC) as presented in Table 5 (to accept zero results in the calculation a value of 0.01 is added to both the numerator and denominator). Donors with samples possessing a CBD to THC metabolite ratio in excess of 10 are highly likely to be exclusive CBD users. Donors with samples possessing a CBD to THC metabolite ratio of less than one (THCs exceed CBDs) are either marijuana users or mixed users. Donors with samples possessing a CBD to THC metabolite ratio between one and ten are inconclusive. With larger data sets, the breadth of the inconclusive bin is expected to diminish. Conditional formatting of the calculated metabolic ratio indicates the identified use category. In the "Call" column, CBD indicates CBD use; MARIJUANA indicates marijuana use; INCONCLUSIVE indicates inconclusive results; ND indicates no markers detected.

TABLE 5

Measured Metabolite Levels and CBD to THC Metabolite Ratio

| Sample # | THC (ng/mL) | CBD (ng/mL) | COO-THC (ng/mL) | COO-CBD (ng/mL) | CBDs/ THCs [1] | CALL |
|---|---|---|---|---|---|---|
| 1 | | | | | ND | ND |
| 2 | 2.45 | 6.45 | 291.06 | 38.02 | 0.15 | MARIJUANA |
| 3 | | 2.76 | 7.05 | | 0.39 | MARIJUANA |
| 4 | | | | | ND | ND |
| 5 | 15.97 | 23.84 | 1425.05 | 20.19 | 0.03 | MARIJUANA |
| 6 | 0.20 | | 108.34 | | 0.00 | MARIJUANA |
| 7 | | | | | ND | ND |
| 8 | | | 2.94 | | 0.00 | MARIJUANA |
| 9 | | 1.33 | | | 134.00 | CBD |
| 10 | | 390.65 | 3.12 | 392.84 | 250.32 | CBD |
| 11 | | | | | ND | ND |
| 12 | 2.29 | 5.97 | 320.76 | 35.72 | 0.13 | MARIJUANA |
| 13 | | 2.86 | 7.87 | 3.81 | 0.85 | MARIJUANA |
| 14 | | | | | ND | ND |
| 15 | 11.75 | 20.59 | 1593.47 | 46.45 | 0.04 | MARIJUANA |
| 16 | 0.18 | | 128.58 | | 0.00 | MARIJUANA |
| 17 | | | | | ND | ND |

TABLE 5-continued

Measured Metabolite Levels and CBD to THC Metabolite Ratio

| Sample # | THC (ng/mL) | CBD (ng/mL) | COO-THC (ng/mL) | COO-CBD (ng/mL) | CBDs/ THCs [1] | CALL |
|---|---|---|---|---|---|---|
| 18 | | | 3.52 | | 0.00 | MARIJUANA |
| 19 | | 1.40 | | | 141.00 | CBD |
| 20 | | 410.00 | | 508.55 | 91856.00 | CBD |
| 21 | | 30.31 | | 45.97 | 7629.00 | CBD |
| 22 | | 5.11 | 3.37 | 63.95 | 20.43 | CBD |
| 23 | | 30.96 | 4.71 | 58.87 | 19.03 | CBD |
| 24 | | 5.10 | 5.02 | 98.04 | 20.51 | CBD |
| 25 | | 5.74 | 10.84 | 85.47 | 8.41 | INCONCLUSIVE |
| 26 | | | | 13.65 | 1366.00 | CBD |
| 27 | 0.16 | 332.56 | 27.72 | 180.8 | 18.41 | CBD |
| 28 | | 4.46 | 0.89 | 46.6 | 56.74 | CBD |
| 29 | | 7.74 | | | 775.00 | CBD |
| 30 | | 6.07 | 1.28 | 15.82 | 16.98 | CBD |
| 31 | 0.35 | 121.62 | 11.48 | 50.52 | 14.54 | CBD |
| 32 | | 513.20 | | 212.88 | 72609.00 | CBD |
| 33 | | 6.19 | 10.49 | 91.74 | 9.33 | INCONCLUSIVE |
| 34 | | 15.88 | | 28.99 | 4488.00 | CBD |
| 35 | | 21.14 | | 72.81 | 9396.00 | CBD |
| 36 | | 13.60 | | 54.62 | 6823.00 | CBD |
| 37 | | 53.89 | | 53.01 | 10691.00 | CBD |
| 38 | | 38.46 | 5.25 | 34.26 | 13.83 | CBD |
| 39 | | 131.17 | | 47.50 | 17868.00 | CBD |
| 40 | 2.14 | 354.96 | 44.91 | 102.78 | 9.73 | INCONCLUSIVE |
| 41 | | | | | ND | ND |
| 42 | | 246.75 | 77.19 | 79.56 | 4.23 | INCONCLUSIVE |
| 43 | | 4.25 | | 20.63 | 2489.00 | CBD |
| 44 | | | 40.28 | | 0.00 | MARIJUANA |
| 45 | | 68.80 | 0.86 | 23.66 | 106.29 | CBD |
| 46 | | 22.32 | 27.99 | 104.71 | 4.54 | INCONCLUSIVE |
| 47 | 1.99 | 1331.32 | 19.75 | 497.41 | 84.08 | CBD |
| 48 | 1.07 | 0.23 | 495.36 | | 0.00 | MARIJUANA |
| 49 | | | | | ND | ND |
| 50 | | | | | ND | ND |
| 51 | | 0.97 | | | 98.00 | CBD |
| 52 | | | | | ND | ND |
| 53 | | 17.74 | 4.99 | 16.61 | 6.87 | INCONCLUSIVE |
| 54 | | | | | ND | ND |
| 55 | | | | | ND | ND |
| 56 | | 33.32 | 4.26 | 26.10 | 13.92 | CBD |
| 57 | | 1.10 | 20.20 | 5.56 | 0.33 | MARIJUANA |
| 58 | | 16.19 | 25.74 | 46.60 | 2.44 | INCONCLUSIVE |
| 59 | | 1745.67 | 3.20 | 929.19 | 833.29 | CBD |
| 60 | | 40.60 | | 31.19 | 7180.00 | CBD |
| 61 | | 0.35 | | 4.81 | 517.00 | CBD |
| 62 | | 5.16 | | 25.35 | 3052.00 | CBD |
| 63 | | 17.60 | | 2.36 | 1997.00 | CBD |
| 64 | | | 3.06 | 10.21 | 3.33 | INCONCLUSIVE |
| 65 | | 128.35 | 3.54 | 114.19 | 68.32 | CBD |
| 66 | | 85.31 | 7.45 | 71.42 | 21.01 | CBD |
| 67 | 0.85 | 647.42 | 60.76 | 319.58 | 15.69 | CBD |
| 68 | | 0.49 | | 1.16 | 166.00 | CBD |
| 69 | | 1.32 | | 3.69 | 502.00 | CBD |
| 70 | | | | | ND | ND |
| 71 | | 0.68 | | | 69.00 | CBD |
| 72 | | 5.43 | 2.97 | 79.39 | 28.47 | CBD |
| 73 | 4.51 | 398.66 | 287.88 | 216.67 | 2.10 | INCONCLUSIVE |
| 74 | 39.89 | 13.44 | 719.90 | | 0.02 | MARIJUANA |
| 75 | 48.51 | 2.56 | 4206.67 | 43.15 | 0.01 | MARIJUANA |
| 76 | | 5.88 | 1.09 | 3.36 | 8.41 | INCONCLUSIVE |
| 77 | | 121.39 | 0.93 | 17.83 | 148.12 | CBD |
| 78 | | 8.96 | | 3.44 | 1241.00 | CBD |
| 79 | | 6.28 | | 7.42 | 1371.00 | CBD |
| 80 | | 3.04 | 60.18 | | 0.05 | MARIJUANA |
| 81 | | | | | ND | ND |
| 82 | | 55.94 | 3.18 | 19.98 | 23.80 | CBD |
| 83 | | 1.51 | | 22.58 | 2410.00 | CBD |
| 84 | | 1.15 | | | 116.00 | CBD |
| 85 | | 13.73 | | | 1374.00 | CBD |
| 86 | | 0.68 | | | 69.00 | CBD |
| 87 | | | | | ND | ND |
| 88 | 1.25 | 62.67 | 616.77 | 53.10 | 0.19 | MARIJUANA |
| 89 | 7.59 | 169.41 | 408.31 | 48.31 | 0.52 | MARIJUANA |
| 90 | | | | | ND | ND |
| 91 | | | 3.02 | 10.43 | 3.45 | INCONCLUSIVE |
| 92 | | 0.81 | | 13.45 | 1427.00 | CBD |

TABLE 5-continued

Measured Metabolite Levels and CBD to THC Metabolite Ratio

| Sample # | THC (ng/mL) | CBD (ng/mL) | COO-THC (ng/mL) | COO-CBD (ng/mL) | CBDs/ THCs [1] | CALL |
|---|---|---|---|---|---|---|
| 93 | 0.91 | 2.23 | 150.46 | 7.47 | 0.06 | MARIJUANA |
| 94 | | 38.74 | 10.23 | 104.9 | 14.03 | CBD |
| 95 | | 1.85 | | 12.20 | 1406.00 | CBD |
| 96 | | 63.25 | 44.57 | 73.72 | 3.07 | INCONCLUSIVE |
| 97 | | 8.16 | | 6.84 | 1501.00 | CBD |
| 98 | | 13.51 | | 8.69 | 2221.00 | CBD |
| 99 | | 32.45 | | | 3246.00 | CBD |
| 100 | | 3.05 | | 20.62 | 2368.00 | CBD |
| 101 | | | | | ND | ND |
| 102 | | 4.00 | | | 401.00 | CBD |
| 103 | | 41.10 | 3.67 | 11.15 | 14.20 | CBD |
| 104 | | 3.26 | | 10.43 | 1370.00 | CBD |
| 105 | | 17.48 | | 4.28 | 2177.00 | CBD |
| 106 | | 5.52 | 9.22 | 99.34 | 11.36 | CBD |
| 107 | | 2.70 | | | 271.00 | CBD |
| 108 | | 0.62 | | | 63.00 | CBD |
| 109 | | | | | ND | ND |
| 110 | | 301.08 | 26.02 | 276.49 | 22.19 | CBD |
| 111 | | 0.66 | | | 67.00 | CBD |
| 112 | | 0.56 | | | 57.00 | CBD |
| 113 | | | | | ND | ND |
| 114 | | | | | ND | ND |
| 115 | | 5.10 | | 2.08 | 719.00 | CBD |
| 116 | | 0.59 | | 7.01 | 761.00 | CBD |
| 117 | | 1.29 | | | 130.00 | CBD |
| 118 | | 3.65 | | 50.33 | 5399.00 | CBD |
| 119 | | | | | ND | |
| 120 | | 98.06 | | 166.32 | 26439.00 | CBD |
| 121 | 119.05 | 4.52 | 1864.44 | 24.26 | 0.01 | MARIJUANA |
| 122 | 1.55 | 250.93 | 107.59 | 290.71 | 4.96 | INCONCLUSIVE |
| 123 | | 6.27 | | 18.76 | 2504.00 | CBD |
| 124 | | 0.50 | | | 51.00 | CBD |
| 125 | | 0.78 | | | 79.00 | CBD |
| 126 | | 504.49 | 27.33 | 72.51 | 21.10 | CBD |
| 127 | | 101.51 | 9.60 | 61.52 | 16.97 | CBD |
| 128 | | | | | ND | ND |
| 129 | 0.73 | 24.16 | 3.48 | 14.11 | 9.07 | INCONCLUSIVE |
| 130 | | 2.31 | | | 232.00 | CBD |
| 131 | | 1.25 | 220.15 | 4.99 | 0.03 | MARIJUANA |
| 132 | | 0.79 | | | 80.00 | CBD |
| 133 | | 4.54 | 84.54 | 23.34 | 0.33 | MARIJUANA |
| 134 | | 0.69 | 5.84 | | 0.12 | MARIJUANA |
| 135 | | 19.14 | 1.73 | 80.67 | 57.37 | CBD |
| 136 | | 17.43 | 1.62 | 85.86 | 63.37 | CBD |
| 137 | | | | | ND | ND |
| 138 | 1.20 | 546.07 | 50.33 | 355.08 | 17.48 | CBD |
| 139 | | | 6.63 | | 0.00 | MARIJUANA |
| 140 | | 2.33 | 7.72 | 27.25 | 3.83 | INCONCLUSIVE |
| 141 | | 534.11 | | 86.47 | 62059.00 | CBD |
| 142 | | 59.18 | 5.43 | 70.82 | 23.90 | CBD |
| 143 | | | | | ND | ND |
| 144 | | | | | ND | ND |
| 145 | 1.33 | | | | 0.01 | MARIJUANA |
| 146 | | 10.16 | | 36.2 | 4637.00 | CBD |
| 147 | 1.04 | 3202.27 | 1019.18 | 1360.03 | 4.47 | INCONCLUSIVE |
| 148 | 1.02 | 609.56 | 80.58 | 60.23 | 8.21 | INCONCLUSIVE |
| 149 | | | | | ND | ND |
| 150 | | 5.69 | | 14.82 | 2052.00 | CBD |
| 151 | | | | | ND | ND |
| 152 | | 429.61 | 16.13 | 701.77 | 70.10 | CBD |
| 153 | | 58.9 | | 89.05 | 14796.00 | CBD |
| 154 | | 102.45 | | 238.38 | 34084.00 | CBD |
| 155 | | 147.13 | 4.58 | 145.11 | 63.67 | CBD |
| 156 | | 7.00 | 4.38 | 53.46 | 13.77 | CBD |
| 157 | | 60.50 | 19.90 | 46.52 | 5.38 | INCONCLUSIVE |
| 158 | | | 53.41 | | 0.00 | MARIJUANA |
| 159 | | 5.37 | | 77.92 | 8330.00 | CBD |
| 160 | | 6.00 | 1.18 | 9.81 | 13.29 | CBD |
| 161 | | | 2.90 | | 0.00 | MARIJUANA |
| 162 | | 8.80 | 3.33 | 6.30 | 4.52 | INCONCLUSIVE |
| 163 | 1.23 | | 136.73 | | 0.00 | MARIJUANA |
| 164 | | 6.17 | 1.59 | 23.59 | 18.61 | CBD |
| 165 | | | | | ND | ND |
| 166 | | 10.49 | 17.09 | 46.53 | 3.34 | INCONCLUSIVE |
| 167 | | | | | ND | ND |

TABLE 5-continued

Measured Metabolite Levels and CBD to THC Metabolite Ratio

| Sample # | THC (ng/mL) | CBD (ng/mL) | COO-THC (ng/mL) | COO-CBD (ng/mL) | CBDs/THCs [1] | CALL |
|---|---|---|---|---|---|---|
| 168 | | 4.2 | | 6.91 | 1112.00 | CBD |
| 169 | | 17.58 | | 28.03 | 4562.00 | CBD |
| 170 | 2.54 | | 315.94 | | 0.00 | MARIJUANA |
| 171 | 2.61 | 28.24 | 1873.2 | 135.08 | 0.09 | MARIJUANA |
| 172 | 2.38 | 139.89 | 576.12 | 79.75 | 0.38 | MARIJUANA |
| 173 | | 0.76 | | 15.99 | 1676.00 | CBD |
| 174 | | 1.92 | | 11.16 | 1309.00 | CBD |
| 175 | | 29.48 | | 331.18 | 36067.00 | CBD |
| 176 | | 3.59 | | 34.36 | 3796.00 | CBD |
| 177 | | 1.52 | | 18.08 | 1961.00 | CBD |
| 178 | 32.29 | 0.51 | 333.94 | | 0.00 | MARIJUANA |
| 179 | | 101.31 | | 33.42 | 13474.00 | CBD |
| 180 | | 1.96 | 11.58 | 73.08 | 6.48 | INCONCLUSIVE |
| 181 | | 3.45 | | | 346.00 | CBD |
| 182 | | 7.62 | 6.04 | 9.9 | 2.90 | INCONCLUSIVE |
| 183 | | 90.21 | 25.5 | 198.33 | 11.31 | CBD |
| 184 | | 32.97 | | 17.61 | 5059.00 | CBD |
| 185 | | 59.35 | | 98.69 | 15805.00 | CBD |
| 186 | | 29.83 | | 188.48 | 21832.00 | CBD |
| 187 | | 78.21 | 12.55 | 6.71 | 6.76 | INCONCLUSIVE |
| 188 | | 0.62 | 12.99 | | 0.05 | MARIJUANA |
| 189 | | 9.91 | 30.46 | 78.72 | 2.91 | INCONCLUSIVE |
| 190 | | 1.83 | 10.9 | 33.58 | 3.25 | INCONCLUSIVE |
| 191 | | | | | ND | ND |
| 192 | | | | | ND | ND |
| 193 | | 179.62 | | 51.22 | 23085.00 | CBD |
| 194 | | | 4.6 | | 0.00 | MARIJUANA |
| 195 | | 35.45 | 6.83 | 61.4 | 14.16 | CBD |
| 196 | 0.62 | | 57.88 | | 0.00 | MARIJUANA |
| 197 | | | | | ND | ND |
| 198 | | | | | ND | ND |
| 199 | | | | | ND | ND |
| 200 | 2.06 | 21.42 | | 123.9 | 70.21 | CBD |
| 201 | | 15.57 | | 35 | 5058.00 | CBD |
| 202 | | 13.24 | | 125.61 | 13886.00 | CBD |
| 203 | 0.86 | 251.85 | 21.48 | 171.09 | 18.92 | CBD |
| 204 | | 0.26 | 7.17 | | 0.04 | MARIJUANA |
| 205 | | | | | ND | ND |
| 206 | 14.22 | 0.56 | 1079.42 | | 0.00 | MARIJUANA |
| 207 | | 0.31 | | | 32.00 | CBD |
| 208 | 13.87 | 7.31 | 255.68 | 71.3 | 0.29 | MARIJUANA |
| 209 | | 3.59 | | 16.63 | 2023.00 | CBD |
| 210 | | | | | ND | ND |
| 211 | | 2.4 | | 29.56 | 3197.00 | CBD |
| 212 | | 26.44 | 3.95 | 34.08 | 15.29 | CBD |
| 213 | | 23.44 | 74.45 | 302.9 | 4.38 | INCONCLUSIVE |
| 214 | | 242.25 | 49.43 | 237.69 | 9.71 | INCONCLUSIVE |
| 215 | 21.98 | 221.23 | 2276.25 | 62.17 | 0.12 | MARIJUANA |
| 216 | | 501.83 | 56.08 | 501.42 | 17.89 | CBD |
| 217 | | 13.2 | | 75.39 | 8860.00 | CBD |
| 218 | | 123.82 | 109.01 | 2867.04 | 27.43 | CBD |
| 219 | | 13.02 | 2.56 | 22.9 | 13.98 | CBD |
| 220 | | 13.04 | 8.63 | 131.33 | 16.71 | CBD |
| 221 | | 105.93 | 2.75 | 37.32 | 51.91 | CBD |
| 222 | | 8.04 | 3.44 | 83.72 | 26.60 | CBD |
| 223 | | 127.88 | | 29.69 | 15758.00 | CBD |
| 224 | | 1004.24 | | 109.18 | 111343.00 | CBD |
| 225 | | 30.89 | | 52.43 | 8333.00 | CBD |
| 226 | | 173.18 | | 4.47 | 17766.00 | CBD |
| 227 | | | 7.73 | | 0.00 | MARIJUANA |
| 228 | | 48.44 | 4.27 | 74.68 | 28.77 | CBD |
| 229 | | | | | ND | ND |
| 230 | | 17.34 | | 68.33 | 8568.00 | CBD |
| 231 | | | | | ND | ND |
| 232 | | 32.07 | 49.89 | 620.06 | 13.07 | CBD |
| 233 | 12.29 | 2.34 | 426.25 | 8.4 | 0.02 | MARIJUANA |
| 234 | | | | | ND | ND |
| 235 | | | | | ND | ND |
| 236 | | 62.2 | | 65.71 | 12792.00 | CBD |
| 237 | | | | | ND | ND |
| 238 | | | | 9.19 | 920.00 | CBD |
| 239 | | 20.98 | 5.93 | 94.81 | 19.49 | CBD |
| 240 | 6.81 | 6.42 | 82.45 | 21.21 | 0.31 | MARIJUANA |
| 241 | 8.33 | | 2440.11 | 6.02 | 0.00 | MARIJUANA |
| 242 | | | | 8.63 | 864.00 | CBD |

TABLE 5-continued

Measured Metabolite Levels and CBD to THC Metabolite Ratio

| Sample # | THC (ng/mL) | CBD (ng/mL) | COO-THC (ng/mL) | COO-CBD (ng/mL) | CBDs/THCs [1] | CALL |
|---|---|---|---|---|---|---|
| 243 | | | | | ND | ND |
| 244 | | | 7.32 | | 0.00 | MARIJUANA |
| 245 | | | 3.86 | | 0.00 | MARIJUANA |
| 246 | | 9.62 | | 8.55 | 1818.00 | CBD |
| 247 | | | 47.98 | | 0.00 | MARIJUANA |
| 248 | | 14.7 | 4.62 | 23.87 | 8.33 | INCONCLUSIVE |
| 249 | 4.63 | 4.27 | 673.19 | | 0.01 | MARIJUANA |
| 250 | | | | | ND | ND |
| 251 | | 23.61 | | 24.27 | 4789.00 | CBD |
| 252 | | 6.17 | | 23.22 | 2940.00 | CBD |
| 253 | | 1.96 | | 19.1 | 2107.00 | CBD |
| 254 | | 52.87 | | 8.89 | 6177.00 | CBD |
| 255 | | 19.85 | | 84.17 | 10403.00 | CBD |
| 256 | | | | | ND | ND |
| 257 | | 67.16 | 108.86 | 492.02 | 5.14 | INCONCLUSIVE |
| 258 | | 0.76 | | | 77.00 | CBD |
| 259 | | | | | ND | ND |
| 260 | | | | | ND | ND |
| 261 | | | | | ND | ND |
| 262 | | 7.27 | | 11.03 | 1831.00 | CBD |
| 263 | | | | | ND | ND |
| 264 | | | | | ND | ND |
| 265 | | | | | ND | ND |
| 266 | | | | | ND | ND |
| 267 | | | 50.66 | | 0.00 | MARIJUANA |
| 268 | | | | | ND | ND |
| 269 | | | | | ND | ND |
| 270 | | 209.84 | 3.87 | 3.1 | 54.88 | CBD |
| 271 | | | | | ND | ND |
| 272 | | 0.78 | | 2.35 | 314.00 | CBD |
| 273 | | | | | ND | ND |
| 274 | | 7.94 | | 53.27 | 6122.00 | CBD |
| 275 | | 0.83 | | 1.6 | 244.00 | CBD |
| 276 | | 30.18 | | 38.57 | 6876.00 | CBD |
| 277 | | | | | ND | ND |
| 278 | | 4.36 | 6.51 | 21.42 | 3.96 | INCONCLUSIVE |
| 279 | | | | | ND | ND |
| 280 | | 38.02 | | 9.51 | 4754.00 | CBD |
| 281 | 38.62 | 2.67 | 782.86 | 16.01 | 0.02 | MARIJUANA |
| 282 | | | 79.04 | | 0.00 | MARIJUANA |
| 283 | 5.55 | 0.69 | 1484.22 | 2.46 | 0.00 | MARIJUANA |
| 284 | | 4.46 | | 97.28 | 10175.00 | CBD |
| 285 | | | | | ND | ND |
| 286 | | 42.88 | 70.85 | 125.57 | 2.38 | INCONCLUSIVE |
| 287 | | | | | ND | ND |
| 288 | | | | | ND | ND |
| 289 | | 1.6 | | 105 | 10661.00 | CBD |
| 290 | | | 49.61 | | 0.00 | MARIJUANA |
| 291 | | 3.85 | | 4.6 | 846.00 | CBD |
| 292 | | | | | ND | ND |
| 293 | | | | | ND | ND |
| 294 | | | | | ND | ND |
| 295 | | | | | ND | ND |
| 296 | | | | | ND | ND |
| 297 | | 1.32 | | | 133.00 | CBD |
| 298 | | 28.5 | 5.48 | 73 | 18.49 | CBD |
| 299 | | | | | ND | ND |
| 300 | | | | | ND | ND |
| 301 | | 1.33 | 9.11 | 2.74 | 0.45 | MARIJUANA |
| 302 | | 8.79 | 2.99 | 39.39 | 16.06 | CBD |
| 303 | | | 28.84 | | 0.00 | MARIJUANA |
| 304 | | | | | ND | ND |
| 305 | | | | | ND | ND |
| 306 | 29.41 | 4.76 | 2000.49 | | 0.00 | MARIJUANA |
| 307 | | 73.78 | 31.6 | 327.05 | 12.68 | CBD |
| 308 | | | | | ND | ND |
| 309 | | | | | ND | ND |
| 310 | | | | | ND | ND |
| 311 | | | | | ND | ND |
| 312 | | | | | ND | ND |
| 313 | | 37.01 | 56.04 | 9.57 | 0.83 | MARIJUANA |
| 314 | | | | | ND | ND |
| 315 | | | | | ND | ND |
| 316 | | | | | ND | ND |
| 317 | | 7.97 | 309.78 | 36.23 | 0.14 | MARIJUANA |

TABLE 5-continued

Measured Metabolite Levels and CBD to THC Metabolite Ratio

| Sample # | THC (ng/mL) | CBD (ng/mL) | COO-THC (ng/mL) | COO-CBD (ng/mL) | CBDs/ THCs [1] | CALL |
|---|---|---|---|---|---|---|
| 318 | | | | | ND | ND |
| 319 | | | 325.62 | 5.75 | 0.02 | MARIJUANA |
| 320 | | | | | ND | ND |
| 321 | | | | | ND | ND |
| 322 | | | | | ND | ND |
| 323 | | | | | ND | ND |
| 324 | | | | | ND | ND |
| 325 | | 3.66 | 5.29 | 30.39 | 6.43 | INCONCLUSIVE |
| 326 | | 87.25 | 3.13 | 7.1 | 30.05 | CBD |
| 327 | | 20.48 | 4.05 | 185.37 | 50.70 | CBD |

[1] To mathematically accept "zero results" a value of 0.01 was added to both the numerator and denominator.

Figure 8:
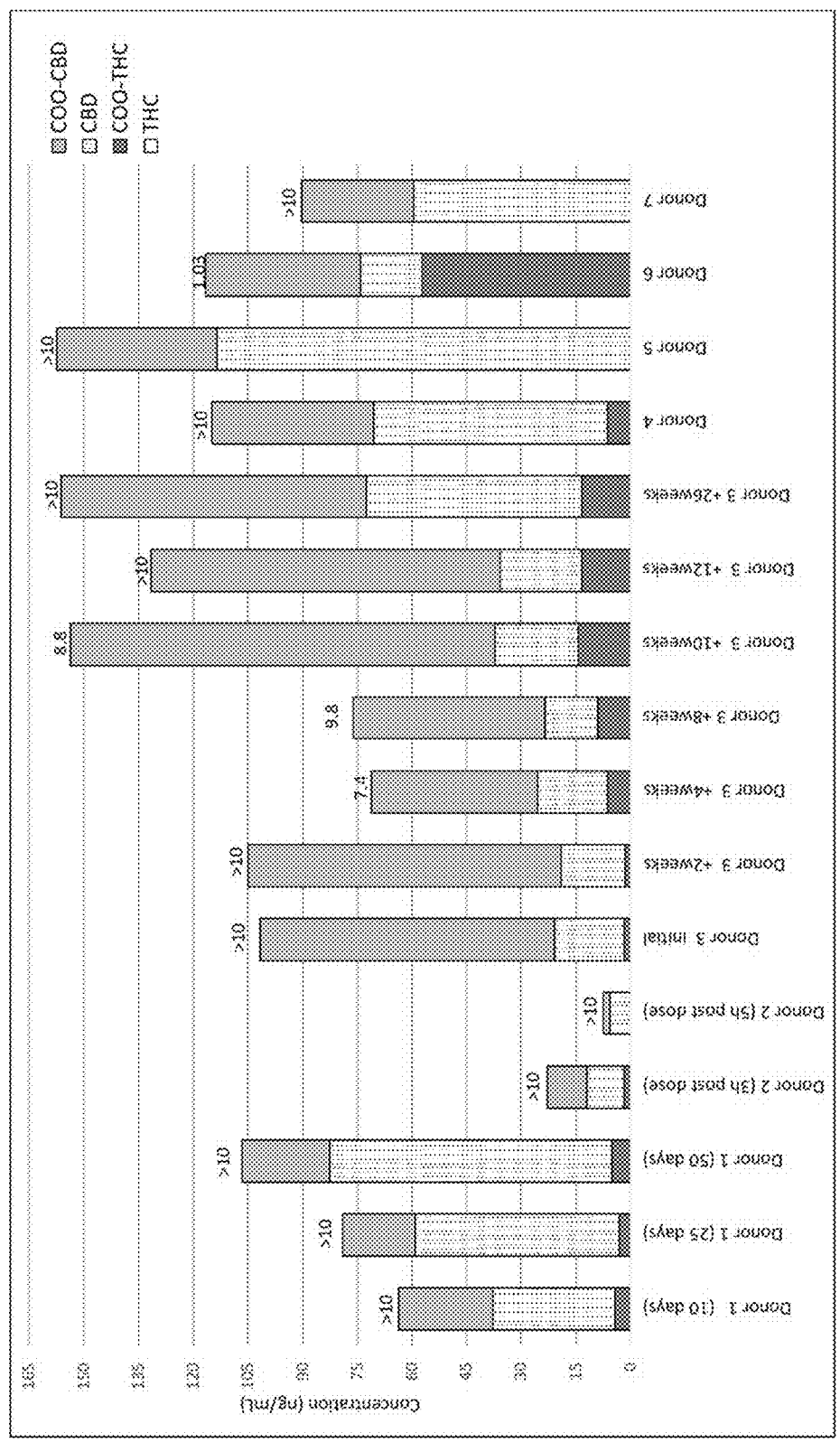
FIG. 8 shows cannabinoid metabolite profiles from trusted CBD donors in accordance with an embodiment of the disclosure.

Seven donors known to be CBD users and known to abstain from marijuana use provided unambiguous samples sets. Donor 1 was taking a daily dose of 21 mg CBD contaminated with 0.5 mg of THC (as measured by the laboratory). Donor 2 provided two samples at 3 and 5 hours post dose; the CBD dosage strength and level of THC contamination is unknown. Donor 3 was a long-term CBD user and had recently switched to a product containing a THC contamination of 0.07% relative to the CBD content. Donors 4, 5, and 7 were taking a 30 mg CBD capsule for 20-30 days. Donor 6 was using a CBD vape for 6 months. Hydrolyzed cannabinoid metabolites were measured in each of the donated samples (FIG. 8). Thirteen of sixteen samples contained detectible carboxy-THC; however, all but one was less than 15 ng/mL. Parent THC was not detected in any of these samples. Numbers above each bar in FIG. 8 is the CBD/THC ratio. Twelve samples had ratios greater than 10, or in the CBD group. The other four samples had ratios ranging from 1 to 9.8 within the indeterminate group.

The final group of data is from samples that were ordered from clients. During the first months of production 169 samples were received for CBD/THC ratio testing. Nearly one third of samples (32.5%) were negative for both CBD and THC metabolites (Table 6). Another third had ratios less than 1, which placed them in the marijuana group, 24.3% were reported as consistent with CBD use (ratios greater than 10), and 10% were indeterminate with ratios greater than 1 but less than 10.

TABLE 6

Measured Metabolite Levels and CBD to THC Metabolite Ratio - Production Samples

| Sample # | CBD (ng/mL) | COO-CBD (ng/mL) | THC (ng/mL) | COO-THC (ng/mL) | CBDs/ THCs [1] | CALL |
|---|---|---|---|---|---|---|
| 1 | 0 | 0 | 0 | 0 | ND | ND |
| 2 | 19 | 43.1 | 0 | 3.1 | 19.97 | CBD |
| 3 | 0 | 0 | 0 | 5.2 | 0.00 | MARIJUANA |
| 4 | 0 | 0 | 0 | 12.4 | 0.00 | MARIJUANA |
| 5 | 0 | 0 | 0 | 0 | ND | ND |
| 6 | 1266.4 | 5000 | 0 | 0 | 626641.00 | CBD |
| 7 | 4.3 | 6 | 1.8 | 105.9 | 0.10 | MARIJUANA |
| 8 | 0 | 0 | 0 | 6.6 | 0.00 | MARIJUANA |
| 9 | 0 | 0 | 0 | 0 | ND | ND |
| 10 | 3.9 | 13 | 0 | 25.1 | 0.67 | MARIJUANA |
| 11 | 0 | 0 | 0 | 17.4 | 0.00 | MARIJUANA |
| 12 | 19.2 | 127.2 | 0 | 30.1 | 4.86 | INDETERMINATE |
| 13 | 0 | 0 | 0 | 0 | ND | ND |
| 14 | 0 | 0 | 0 | 0 | ND | ND |
| 15 | 0 | 0 | 0 | 0 | ND | ND |
| 16 | 0 | 0 | 0 | 0 | ND | ND |
| 17 | 0 | 0 | 0 | 35.8 | 0.00 | MARIJUANA |
| 18 | 0 | 0 | 0 | 0 | ND | ND |
| 19 | 0 | 0 | 0 | 0 | ND | ND |
| 20 | 0 | 0 | 0 | 0 | ND | ND |
| 21 | 0 | 0 | 0 | 0 | ND | ND |
| 22 | 7.9 | 213.2 | 0 | 13 | 17.00 | CBD |
| 23 | 73 | 71.4 | 0 | 6.3 | 22.89 | CBD |
| 24 | 99.4 | 63.8 | 0 | 15.5 | 10.52 | CBD |
| 25 | 0 | 0 | 0 | 0 | ND | ND |
| 26 | 0 | 0 | 0 | 0 | ND | ND |
| 27 | 0 | 0 | 0 | 4 | 0.00 | MARIJUANA |
| 28 | 0 | 0 | 0 | 16.1 | 0.00 | MARIJUANA |
| 29 | 0 | 0 | 0 | 0 | ND | ND |
| 30 | 0 | 0 | 0 | 0 | ND | ND |
| 31 | 5.9 | 0 | 41.4 | 1073.5 | 0.01 | MARIJUANA |
| 32 | 41.7 | 28.7 | 0 | 13.2 | 5.33 | INDETERMINATE |
| 33 | 0 | 0 | 6.3 | 604 | 0.00 | MARIJUANA |
| 34 | 44.2 | 255.3 | 0 | 0 | 29951.00 | CBD |
| 35 | 0 | 0 | 0 | 0 | ND | ND |

TABLE 6-continued

Measured Metabolite Levels and CBD to THC Metabolite Ratio - Production Samples

| Sample # | CBD (ng/mL) | COO-CBD (ng/mL) | THC (ng/mL) | COO-THC (ng/mL) | CBDs/ THCs [1] | CALL |
|---|---|---|---|---|---|---|
| 36 | 0 | 0 | 0 | 0 | ND | ND |
| 37 | 0 | 0 | 0 | 0 | ND | ND |
| 38 | 0 | 0 | 0 | 0 | ND | ND |
| 39 | 0 | 0 | 0 | 14.3 | 0.00 | MARIJUANA |
| 40 | 2.1 | 0 | 9.4 | 988.5 | 0.00 | MARIJUANA |
| 41 | 0 | 0 | 0 | 37.6 | 0.00 | MARIJUANA |
| 42 | 0 | 0 | 0 | 20 | 0.00 | MARIJUANA |
| 43 | 0 | 0 | 0 | 10.4 | 0.00 | MARIJUANA |
| 44 | 0 | 0 | 0 | 17 | 0.00 | MARIJUANA |
| 45 | 341.6 | 276.1 | 2.2 | 20.5 | 27.20 | CBD |
| 46 | 99.2 | 164.5 | 0 | 9.1 | 28.95 | CBD |
| 47 | 0 | 0 | 0 | 0 | ND | ND |
| 48 | 0 | 0 | 0 | 0 | ND | ND |
| 49 | 0 | 0 | 0 | 0 | ND | ND |
| 50 | 0 | 0 | 0 | 0 | ND | ND |
| 51 | 679 | 927.1 | 0 | 0 | 160611.00 | CBD |
| 52 | 0.98 | 3.3 | 0 | 0 | 429.00 | CBD |
| 53 | 0 | 0 | 0 | 0 | ND | ND |
| 54 | 0 | 0 | 0 | 0 | ND | ND |
| 55 | 0 | 0 | 0 | 0 | ND | ND |
| 56 | 0 | 0 | 1.9 | 186 | 0.00 | MARIJUANA |
| 57 | 1153.7 | 263.5 | 7.8 | 617 | 2.27 | INDETERMINATE |
| 58 | 0.7 | 1.5 | 0 | 1.9 | 1.16 | INDETERMINATE |
| 59 | 0 | 0 | 0 | 0 | ND | ND |
| 60 | 327.2 | 306.3 | 0 | 11.5 | 55.04 | CBD |
| 61 | 0 | 0 | 0 | 0 | ND | ND |
| 62 | 0 | 0 | 0 | 0 | ND | ND |
| 63 | 0 | 0 | 0 | 0 | ND | ND |
| 64 | 9.3 | 88.8 | 0 | 22.9 | 4.28 | INDETERMINATE |
| 65 | 0.9 | 0 | 2.6 | 794.4 | 0.00 | MARIJUANA |
| 66 | 30 | 220.4 | 0 | 16 | 15.64 | CBD |
| 67 | 247.4 | 396 | 0 | 40.3 | 15.96 | CBD |
| 68 | 0 | 0 | 0 | 7.5 | 0.00 | MARIJUANA |
| 69 | 0 | 0 | 0 | 19.1 | 0.00 | MARIJUANA |
| 70 | 0.8 | 0 | 0 | 32.5 | 0.02 | MARIJUANA |
| 71 | 24.5 | 222.2 | 0 | 19.6 | 12.58 | CBD |
| 72 | 0 | 0 | 0 | 0 | ND | ND |
| 73 | 0 | 0 | 0 | 19.9 | 0.00 | MARIJUANA |
| 74 | 0.6 | 37.9 | 0 | 0 | 3851.00 | CBD |
| 75 | 1 | 0 | 0 | 0 | 101.00 | CBD |
| 76 | 0 | 0 | 0 | 0 | ND | ND |
| 77 | 0 | 3.7 | 4.6 | 221.3 | 0.02 | MARIJUANA |
| 78 | 6.2 | 23.2 | 6.7 | 1137.2 | 0.03 | MARIJUANA |
| 79 | 0 | 0 | 0 | 97 | 0.00 | MARIJUANA |
| 80 | 74.6 | 90.5 | 0 | 21.5 | 7.68 | INDETERMINATE |
| 81 | 0 | 0 | 0 | 0 | ND | ND |
| 82 | 0 | 0 | 0 | 24.2 | 0.00 | MARIJUANA |
| 83 | 0 | 0 | 1.5 | 97.5 | 0.00 | MARIJUANA |
| 84 | 187.5 | 436.1 | 1.1 | 21.1 | 28.08 | CBD |
| 85 | 0 | 0 | 3.2 | 322.3 | 0.00 | MARIJUANA |
| 86 | 260.3 | 28.6 | 0 | 12.8 | 22.55 | CBD |
| 87 | 245.7 | 113.3 | 0 | 0 | 35901.00 | CBD |
| 88 | 675.8 | 111.8 | 0 | 19.4 | 40.58 | CBD |
| 89 | 74.5 | 106.7 | 0 | 13.4 | 13.51 | CBD |
| 90 | 0 | 0 | 0 | 0 | ND | ND |
| 91 | 16.1 | 51.6 | 0 | 3.9 | 17.32 | CBD |
| 92 | 104.6 | 110.2 | 0 | 17.7 | 12.13 | CBD |
| 93 | 13.7 | 0 | 0.6 | 50 | 0.27 | MARIJUANA |
| 94 | 0 | 0 | 0 | 0 | ND | ND |
| 95 | 0 | 0 | 0 | 0 | ND | ND |
| 96 | 0 | 0 | 0 | 10.1 | 0.00 | MARIJUANA |
| 97 | 0 | 0 | 0 | 9.6 | 0.00 | MARIJUANA |
| 98 | 1.5 | 5.7 | 0 | 0 | 721.00 | CBD |
| 99 | 55 | 218.9 | 1.1 | 48 | 5.58 | INDETERMINATE |
| 100 | 3.6 | 0 | 0 | 5.4 | 0.67 | MARIJUANA |
| 101 | 94.5 | 511.2 | 0 | 30.9 | 19.60 | CBD |
| 102 | 78.4 | 510.3 | 0 | 0 | 58871.00 | CBD |
| 103 | 0 | 0 | 0 | 15.6 | 0.00 | MARIJUANA |
| 104 | 1 | 0 | 0.6 | 0 | 1.66 | INDETERMINATE |
| 105 | 0 | 0 | 0 | 0 | ND | ND |
| 106 | 0 | 0 | 0 | 0 | ND | ND |
| 107 | 26.7 | 41.6 | 0.7 | 8.2 | 7.67 | INDETERMINATE |
| 108 | 8.6 | 13.1 | 0 | 0 | 2171.00 | CBD |
| 109 | 0 | 0 | 1.2 | 13.9 | 0.00 | MARIJUANA |
| 110 | 0 | 0 | 0 | 0 | ND | ND |

TABLE 6-continued

Measured Metabolite Levels and CBD to THC Metabolite Ratio - Production Samples

| Sample # | CBD (ng/mL) | COO-CBD (ng/mL) | THC (ng/mL) | COO-THC (ng/mL) | CBDs/THCs [1] | CALL |
|---|---|---|---|---|---|---|
| 111 | 0 | 0 | 0 | 0 | ND | ND |
| 112 | 230.2 | 357.9 | 0 | 30.7 | 19.15 | CBD |
| 113 | 1.4 | 4.9 | 0 | 0 | 631.00 | CBD |
| 114 | 0 | 0 | 0 | 26.8 | 0.00 | MARIJUANA |
| 115 | 0 | 0 | 0 | 0 | ND | ND |
| 116 | 8.7 | 115.8 | 0 | 4.2 | 29.57 | CBD |
| 117 | 2.6 | 0 | 0 | 18 | 0.14 | MARIJUANA |
| 118 | 0 | 0 | 0 | 28.4 | 0.00 | MARIJUANA |
| 119 | 2.3 | 40.1 | 0 | 17.1 | 2.48 | INDETERMINATE |
| 120 | 1.9 | 0 | 5.1 | 204.1 | 0.01 | MARIJUANA |
| 121 | 0 | 0 | 0 | 0 | ND | ND |
| 122 | 25.4 | 286.9 | 0 | 83.2 | 3.75 | INDETERMINATE |
| 123 | 0 | 0 | 0 | 0 | ND | ND |
| 124 | 0 | 4.5 | 0 | 0 | 451.00 | CBD |
| 125 | 155.2 | 70.5 | 0 | 23.1 | 9.77 | INDETERMINATE |
| 126 | 121.4 | 589 | 2.9 | 78.3 | 8.75 | INDETERMINATE |
| 127 | 225.1 | 167.1 | 0 | 16.5 | 23.76 | CBD |
| 128 | 319.2 | 852.5 | 0 | 0 | 117171.00 | CBD |
| 129 | 0 | 0 | 0 | 0 | ND | ND |
| 130 | 0 | 0 | 0.8 | 77.3 | 0.00 | MARIJUANA |
| 131 | 0 | 0 | 0 | 0 | ND | ND |
| 132 | 0 | 0 | 0 | 11.6 | 0.00 | MARIJUANA |
| 133 | 88.2 | 68.1 | 0 | 16.6 | 9.41 | INDETERMINATE |
| 134 | 0.6 | 0 | 3.6 | 988.3 | 0.00 | MARIJUANA |
| 135 | 67.4 | 251.4 | 0 | 35 | 9.11 | INDETERMINATE |
| 136 | 88.2 | 400.1 | 1.8 | 17.5 | 25.29 | CBD |
| 137 | 1.3 | 0 | 0 | 0 | 131.00 | CBD |
| 138 | 0 | 0 | 0 | 10.8 | 0.00 | MARIJUANA |
| 139 | 0 | 0 | 0 | 0 | ND | ND |
| 140 | 0 | 0 | 0 | 0 | ND | ND |
| 141 | 0 | 0 | 0 | 3.9 | 0.00 | MARIJUANA |
| 142 | 0 | 0 | 0 | 0 | ND | ND |
| 143 | 21.3 | 212.5 | 0 | 6 | 38.90 | CBD |
| 144 | 0 | 0 | 0 | 0 | ND | ND |
| 145 | 0 | 0 | 0 | 0 | ND | ND |
| 146 | 0 | 0 | 0 | 33 | 0.00 | MARIJUANA |
| 147 | 1.2 | 0 | 0 | 0 | 121.00 | CBD |
| 148 | 148 | 153.9 | 0 | 6.4 | 47.10 | CBD |
| 149 | 169.4 | 104.4 | 0 | 10.2 | 26.82 | CBD |
| 150 | 0 | 0 | 0 | 0 | ND | ND |
| 151 | 0 | 0 | 1.3 | 95.3 | 0.00 | MARIJUANA |
| 152 | 179.5 | 131.7 | 0 | 5.2 | 59.73 | CBD |
| 153 | 0 | 0 | 0 | 14.7 | 0.00 | MARIJUANA |
| 154 | 0 | 0 | 0 | 14.5 | 0.00 | MARIJUANA |
| 155 | 0 | 0 | 0 | 0 | ND | ND |
| 156 | 13.1 | 6.9 | 0 | 4.9 | 4.08 | INDETERMINATE |
| 157 | 0 | 0 | 0 | 0 | ND | ND |
| 158 | 0 | 0 | 0 | 37.4 | 0.00 | MARIJUANA |
| 159 | 0 | 0 | 0 | 0 | ND | ND |
| 160 | 0 | 0 | 0 | 0 | ND | ND |
| 161 | 0 | 0 | 0 | 10.4 | 0.00 | MARIJUANA |
| 162 | 3.2 | 0 | 34.5 | 462.1 | 0.01 | MARIJUANA |
| 163 | 0.8 | 0 | 0 | 20.1 | 0.04 | MARIJUANA |
| 164 | 0 | 0 | 0 | 48.4 | 0.00 | MARIJUANA |
| 165 | 3.1 | 81.2 | 0 | 61.8 | 1.36 | INDETERMINATE |
| 166 | 0 | 0 | 0 | 16.4 | 0.00 | MARIJUANA |
| 167 | 0 | 0 | 0 | 4.7 | 0.00 | MARIJUANA |
| 168 | 0 | 0 | 0 | 16.9 | 0.00 | MARIJUANA |
| 169 | 64.8 | 159.3 | 0 | 10.9 | 20.54 | CBD |

[1] To mathematically accept "zero results" a value of 0.01 was added to both the numerator and denominator.

Example 3—Embodiments

A1. A method to measure relative levels of CBD and/or THC or metabolites of CBD and/or THC in a biological sample comprising the steps of:
  (a) measuring CBD and/or at least one CBD metabolite;
  (b) measuring THC and/or at least one THC metabolite;
  (c) determining a ratio of the amount of the CBD and/or at least one CBD metabolite to the amount of the THC and/or at least one THC metabolite for the sample.

A2. The method of any of the previous or subsequent embodiments, wherein the measuring of the CBD and/or at least one CBD metabolite and the THC and the at least one THC metabolite is performed by LC-MS/MS.

A3. A method to measure relative levels of CBD and/or THC or metabolites of CBD and/or THC in a biological sample comprising the steps of:
  (a) obtaining MS/MS data comprising a predetermined MS/MS transition for THC and/or at least one THC metabolite and CBD and/or at least one CBD metabolite, wherein the predetermined MS/MS transition comprises a transition for at least one predefined precursor ion of defined m/z and at least one quantitative fragment ion of a defined m/z for each of the THC and/or at least one THC metabolite and the CBD and/or at least one CBD metabolite;
  (b) determining the amount of the THC and/or at least one THC metabolite and the CBD and/or at least one CBD metabolite in the biological sample based on the transitions in step (a); and
  (c) determining a ratio of the amount of the CBD and/or at least one CBD metabolite to the amount of the THC and/or at least one THC metabolite for the biological sample.

A4. The method of any of the previous or subsequent embodiments, wherein the predetermined MS/MS transitions of step (a) further comprise at least one qualitative fragment ion of a defined m/z for each of the THC and/or at least one THC metabolite and the CBD and/or at least one CBD metabolite, and step (b) further comprises determining a transition for the predetermined precursor ion to the at least one qualitative fragment ion for the THC and/or at least one THC metabolite and the CBD and/or at least one CBD metabolite.

A5. The method of any of the previous or subsequent embodiments, wherein the transition for at least one precursor ion to at least one qualitative fragment ion is used to confirm the identity of the THC and/or at least one THC metabolite and the CBD and/or at least one CBD metabolite in the sample.

A6. The method of any of the previous or subsequent embodiments, further comprising identifying the biological sample as being from a subject who has ingested THC and/or CBD and/or is indeterminate for ingesting either THC and/or CBD based on the ratio of the amount of CBD and/or at least one CBD metabolite to the amount of THC and/or at least one THC metabolite for the sample.

A7. The method of any of the previous or subsequent embodiments, wherein the at least one CBD metabolite comprises 7-carboxy-CBD (COO-CBD).

A8. The method of any of the previous or subsequent embodiments, wherein the CBD comprises CBD released from CBD-glucuronide.

A9. The method of any of the previous or subsequent embodiments, wherein the COO-CBD comprises COO-CBD released from 7-carboxy CBD glucuronide.

A10. The method of any of the previous or subsequent embodiments, wherein the at least one THC metabolite comprises 11-carboxy Δ9-THC (COO-THC).

A11. The method of any of the previous or subsequent embodiments, wherein the THC comprises THC released from Δ9-THC-glucuronide.

A12. The method of any of the previous or subsequent embodiments, wherein the COO-THC comprises COO-THC released from 11-carboxy Δ9-THC glucuronide.

A13. The method of any of the previous or subsequent embodiments, wherein the predefined precursor ion of defined m/z comprises at least one of:
  315.1 m/z for THC;
  315.1 m/z for CBD;
  345.1 m/z for COO-THC; and
  345.1 m/z for COO-CBD.

A14. The method of any of the previous or subsequent embodiments, wherein the predefined quantitative fragment ion of defined m/z comprises at least one of:
  193.1 m/z for THC;
  193.1 m/z for CBD;
  193.1 m/z for COO-THC; and
  193.1 m/z for COO-CBD.

A15. The method of any of the previous or subsequent embodiments, wherein the predefined qualitative fragment ion of defined m/z comprises at least one of:
  123.1 m/z and/or 259.1 m/z and 135.1 m/z for THC;
  123.1 m/z and/or 259.1 m/z and 135.1 m/z for CBD;
  299.1 m/z and/or 187.1 m/z and 229.1 m/z for COO-THC; and
  299.1 m/z and/or 257.1 m/z and 229.1 m/z for COO-CBD.

A16. The method of any of the previous or subsequent embodiments, further comprising the use of a labeled isotope internal standard.

A17. The method of any of the previous or subsequent embodiments, wherein the internal standard comprises at least one of $D_3$-THC, $D_3$-CBD, or $D_9$-COO-THC.

A18. The method of the previous or subsequent embodiments, wherein the internal standard $D_9$-COO-THC is used in the measurement of COO-THC and/or COO-CBD.

A19. The method of any of the previous or subsequent embodiments, further comprising at least one of a predefined precursor ion of 318.1 m/z for at least one of $D_3$-THC and/or $D_3$-CBD and a predefined precursor ion of 354.3 m/z for $D_9$-COO-THC.

A20. The method of any of the previous or subsequent embodiments, further comprising at least one of a predefined quantitative fragment ion of 196.2 m/z for at least one of $D_3$-THC and/or $D_3$-CBD and a predefined quantitative fragment ion of 196.1 m/z for $D_9$-COO-THC.

A21. The method of any of the previous or subsequent embodiments, further comprising at least one of a predefined qualitative fragment ion of 123.1 m/z for at least one of $D_3$-THC and/or $D_3$-CBD and a predefined qualitative fragment ion of 308.2 m/z for $D_9$-COO-THC.

A22. The method of any of the previous or subsequent embodiments, wherein the THC and/or at least one THC metabolite and the CBD and/or at least one CBD metabolite exhibit different multiple reaction monitoring retention times.

A23. The method of any of the previous or subsequent embodiments, wherein a ratio of greater than 10 for CBD and/or at least one CBD metabolite as compared to THC and/or at least one THC metabolite indicates CBD use.

A24. The method of any of the previous or subsequent embodiments, wherein a ratio of less than 1.0 for CBD and/or at least one CBD metabolite as compared to THC and/or at least one THC metabolite indicates THC use.

A25. The method of any of the previous or subsequent embodiments, wherein the biological sample is urine.

A26. The method of any of the previous or subsequent embodiments, wherein the determining a ratio of the amount of the CBD and/or at least one CBD metabolite to the amount of the THC and/or at least one THC metabolite for the sample is performed on a computer.

A27. The method of any of the previous or subsequent embodiments, wherein the method distinguishes CBD use from THC use in a subject.

B1. A system comprising:
one or more computers; and
a non-transitory computer readable storage medium containing instructions which, when executed on the one or more computers, cause the one or more computers to perform actions for performing the methods or running any of the systems of any of the previous and/or subsequent embodiments.

B2. A system to measure relative levels of CBD and/or THC or metabolites of CBD and/or THC in a biological sample comprising:
one or more computers; and
a non-transitory computer readable storage medium containing instructions which, when executed on the one or more computers, cause the one or more computers to perform actions comprising at least one of the following steps:
(a) measuring CBD and/or at least one CBD metabolite;
(b) measuring THC and/or at least one THC metabolite;
(c) determining a ratio of the amount of the CBD and/or at least one CBD metabolite to the amount of the THC and/or at least one THC metabolite for the sample.

B3. The system of any of the previous or subsequent embodiments, wherein the measuring of the CBD and/or at least one CBD metabolite and the THC and the at least one THC metabolite is performed by LC-MS/MS.

B4. A system to measure relative levels of CBD and/or THC or metabolites of CBD and/or THC in a biological sample comprising:
(a) a station for obtaining MS/MS data comprising a predetermined MS/MS transition for THC and/or at least one THC metabolite and CBD and/or at least one CBD metabolite, wherein the predetermined MS/MS transition comprises a transition for at least one predefined precursor ion of defined m/z and at least one quantitative fragment ion of a defined m/z for each of the THC and/or at least one THC metabolite and the CBD and/or at least one CBD metabolite;
(b) a station for determining the amount of the THC and/or at least one THC metabolite and the CBD and/or at least one CBD metabolite in the biological sample based on the transitions in step (a); and
(c) a station for determining a ratio of the amount of the CBD and/or at least one CBD metabolite to the amount of the THC and/or at least one THC metabolite for the biological sample.

B5. The system of any of the previous or subsequent embodiments, wherein the predetermined MS/MS transitions of step (a) further comprise at least one qualitative fragment ion of a defined m/z for each of the THC and/or at least one THC metabolite and the CBD and/or at least one CBD metabolite, and step (b) further comprises determining a transition for the predetermined precursor ion to the at least one qualitative fragment ion for the THC and/or at least one THC metabolite and the CBD and/or at least one CBD metabolite.

B6. The system of any of the previous or subsequent embodiments, wherein the transition for at least one precursor ion to at least one qualitative fragment ion is used to confirm the identity of the THC and/or at least one THC metabolite and the CBD and/or at least one CBD metabolite in the sample.

B7. The system of any of the previous or subsequent embodiments, wherein at least one station comprises one or more computers and a non-transitory computer readable storage medium containing instructions which, when executed on the one or more computers, cause the one or more computers to perform an action for the at least one station.

B8. The system of any of the previous or subsequent embodiments, further comprising a station for identifying the sample as being from a subject who has ingested THC and/or CBD and/or is indeterminate for ingesting either THC and/or CBD based on the ratio of the amount of CBD and/or at least one CBD metabolite to the amount of THC and/or at least one THC metabolite for the sample.

B9. The system of any of the previous or subsequent embodiments, wherein the at least one CBD metabolite comprises 7-carboxy-CBD (COO-CBD).

B10. The system of any of the previous or subsequent embodiments, wherein the CBD comprises CBD released from CBD-glucuronide.

B11. The system of any of the previous or subsequent embodiments, wherein the COO-CBD comprises COO-CBD released from 7-carboxy CBD glucuronide.

B12. The system of any of the previous or subsequent embodiments, wherein the at least one THC metabolite comprises 11-carboxy Δ9-THC (COO-THC).

B13. The system of any of the previous or subsequent embodiments, wherein the THC comprises THC released from Δ9-THC-glucuronide.

B14. The system of any of the previous or subsequent embodiments, wherein the COO-THC comprises COO-THC released from 11-carboxy Δ9-THC glucuronide.

B15. The system of any of the previous or subsequent embodiments, wherein the predefined precursor ion of defined m/z comprises at least one of:
315.1 m/z for THC;
315.1 m/z for CBD;
345.1 m/z for COO-THC; and
345.1 m/z for COO-CBD.

B16. The system of any of the previous or subsequent embodiments, wherein the predefined quantitative fragment ion of defined m/z comprises at least one of:
193.1 m/z for THC;
193.1 m/z for CBD;

193.1 m/z for COO-THC; and
193.1 m/z for COO-CBD.

B17. The system of any of the previous or subsequent embodiments, wherein the predefined qualitative fragment ion of defined m/z comprises at least one of:
123.1 m/z and/or 259.1 m/z and 135.1 m/z for THC;
123.1 m/z and/or 259.1 m/z and 135.1 m/z for CBD;
299.1 m/z and/or 187.1 m/z and 229.1 m/z for COO-THC; and
299.1 m/z and/or 257.1 m/z and 229.1 m/z for COO-CBD.

B18. The system of any of the previous or subsequent embodiments, further comprising the use of a labeled isotope internal standard.

B19. The system of any of the previous or subsequent embodiments, wherein the internal standard comprises at least one of $D_3$-THC, $D_3$-CBD, or $D_9$-COO-THC.

B20. The system of any of the previous or subsequent embodiments, wherein the internal standard $D_9$-COO-THC is used in the measurement of COO-THC and/or COO-CBD.

B21. The system of any of the previous or subsequent embodiments, further comprising at least one of a predefined precursor ion of 318.1 m/z for at least one of $D_3$-THC and/or $D_3$-CBD and a predefined precursor ion of 354.3 m/z for $D_9$-COO-THC.

B22. The system of any of the previous or subsequent embodiments, further comprising at least one of a predefined quantitative fragment ion of 196.2 m/z for at least one of $D_3$-THC and/or $D_3$-CBD and a predefined quantitative fragment ion of 196.1 m/z for $D_9$-COO-THC.

B23. The system of any of the previous or subsequent embodiments, further comprising at least one of a predefined qualitative fragment ion of 123.1 m/z for at least one of $D_3$-THC and/or $D_3$-CBD and a predefined qualitative fragment ion of 308.2 m/z for $D_9$-COO-THC.

B24. The system of any of the previous or subsequent embodiments, wherein the THC and/or at least one THC metabolite and the CBD and/or at least one CBD metabolite exhibit different multiple reaction monitoring retention times.

B25. The system of any of the previous or subsequent embodiments, wherein a ratio of greater than 10 for CBD and/or at least one CBD metabolite as compared to THC and/or at least one THC metabolite indicates CBD use.

B26. The system of any of the previous or subsequent embodiments, wherein a ratio of less than 1.0 for CBD and/or at least one CBD metabolite as compared to THC and/or at least one THC metabolite indicates THC use.

B27. The system of any of the previous or subsequent embodiments, wherein the biological sample is urine.

B28. The system of any of the previous or subsequent embodiments, wherein the determining a ratio of the amount of the CBD and/or at least one CBD metabolite to the amount of the THC and/or at least one THC metabolite for the sample is performed on a computer.

B29. The system of any of the previous or subsequent embodiments, wherein the method distinguishes CBD use from THC use in a subject.

C1. A computer-program product tangibly embodied in a non-transitory machine-readable storage medium, including instructions configured to run the systems and/or perform the methods of any of the previous or subsequent embodiments.

C2. A computer-program product tangibly embodied in a non-transitory machine-readable storage medium, including instructions configured to cause one or more computers to perform actions including:
(a) measuring CBD and/or at least one CBD metabolite in a sample;
(b) measuring THC and/or at least one THC metabolite in the sample;
(c) determining a ratio of the amount of the CBD and/or at least one CBD metabolite to the amount of the THC and/or at least one THC metabolite for the sample.

C3. The computer-program product of any of the previous or subsequent embodiments, wherein the measuring of the CBD and/or at least one CBD metabolite and the THC and the at least one THC metabolite is performed by LC-MS/MS.

C4. A computer-program product tangibly embodied in a non-transitory machine-readable storage medium, including instructions configured to cause one or more computers to perform actions to measure relative levels of CBD and/or THC or metabolites of CBD and/or THC in a biological sample comprising at least one of the following steps:
(a) obtaining MS/MS data comprising a predetermined MS/MS transition for THC and/or at least one THC metabolite and CBD and/or at least one CBD metabolite, wherein the predetermined MS/MS transition comprises a transition for at least one predefined precursor ion of defined m/z and at least one quantitative fragment ion of a defined m/z for each of the THC and/or at least one THC metabolite and the CBD and/or at least one CBD metabolite;
(b) determining the amount of the THC and/or at least one THC metabolite and the CBD and/or at least one CBD metabolite in the biological sample based on the transitions in step (a); and
(c) determining a ratio of the amount of the CBD and/or at least one CBD metabolite to the amount of the THC and/or at least one THC metabolite for the biological sample.

C5. The computer-program product of any of the previous or subsequent embodiments, wherein the predetermined MS/MS transitions of step (a) further comprise at least one qualitative fragment ion of a defined m/z for each of the THC and/or at least one THC metabolite and the CBD and/or at least one CBD metabolite, and step (b) further comprises determining a transition for the predetermined precursor ion to the at least one qualitative fragment ion for the THC and/or at least one THC metabolite and the CBD and/or at least one CBD metabolite.

C6. The computer-program product of any of the previous or subsequent embodiments, wherein the transition for at least one precursor ion to at least one qualitative fragment ion is used to confirm the identity of the THC and/or at least one THC metabolite and the CBD and/or at least one CBD metabolite in the sample.

C7. The computer-program product of any of the previous or subsequent embodiments, further comprising instructions configured to cause one or more computers to perform actions including identifying the sample as being from a subject who has ingested THC and/or CBD and/or is indeterminate for ingesting either THC and/or CBD based on the ratio of the amount of CBD and/or at least one CBD metabolite to the amount of THC and/or at least one THC metabolite for the biological sample.

C8. The computer-program product of any of the previous or subsequent embodiments, wherein the at least one CBD metabolite comprises 7-carboxy-CBD (COO-CBD).

C9. The computer-program product of any of the previous or subsequent embodiments, wherein the CBD comprises CBD released from CBD-glucuronide.

C10. The computer-program product of any of the previous or subsequent embodiments, wherein the COO-CBD comprises COO-CBD released from 7-carboxy CBD glucuronide.

C11. The computer-program product of any of the previous or subsequent embodiments, wherein the at least one THC metabolite comprises 11-carboxy Δ9-THC (COO-THC).

C12. The computer-program product of any of the previous or subsequent embodiments, wherein the THC comprises THC released from Δ9-THC-glucuronide.

C13. The computer-program product of any of the previous or subsequent embodiments, wherein the COO-THC comprises COO-THC released from 11-carboxy Δ9-THC glucuronide.

C14. The computer-program product of any of the previous or subsequent embodiments, wherein the predefined precursor ion of defined m/z comprises at least one of:
315.1 m/z for THC;
315.1 m/z for CBD;
345.1 m/z for COO-THC; and
345.1 m/z for COO-CBD.

C15. The computer-program product of any of the previous or subsequent embodiments, wherein the predefined quantitative fragment ion of defined m/z comprises at least one of:
193.1 m/z for THC;
193.1 m/z for CBD;
193.1 m/z for COO-THC; and
193.1 m/z for COO-CBD.

C16. The computer-program product of any of the previous or subsequent embodiments, wherein the predefined qualitative fragment ion of defined m/z comprises at least one of:
123.1 m/z and/or 259.1 m/z and 135.1 m/z for THC;
123.1 m/z and/or 259.1 m/z and 135.1 m/z for CBD;
299.1 m/z and/or 187.1 m/z and 229.1 m/z for COO-THC; and
299.1 m/z and/or 257.1 m/z and 229.1 m/z for COO-CBD.

C17. The computer-program product of any of the previous or subsequent embodiments, further comprising the use of a labeled isotope internal standard.

C18. The computer-program product of any of the previous or subsequent embodiments, wherein the internal standard comprises at least one of $D_3$-THC, $D_3$-CBD, or $D_9$-COO-THC.

C19. The computer-program product of any of the previous or subsequent embodiments, wherein the internal standard $D_9$-COO-THC is used in the measurement of COO-THC and/or COO-CBD.

C20. The computer-program product of any of the previous or subsequent embodiments, further comprising at least one of a predefined precursor ion of 318.1 m/z for at least one of $D_3$-THC and/or $D_3$-CBD and a predefined precursor ion of 354.3 m/z for $D_9$-COO-THC.

C21. The computer-program product of any of the previous or subsequent embodiments, further comprising at least one of a predefined quantitative ion of 196.2 m/z for at least one of $D_3$-THC and/or $D_3$-CBD and a predefined quantitative ion of 196.1 m/z for $D_9$-COO-THC.

C22. The computer-program product of any of the previous or subsequent embodiments, further comprising at least one of a predefined qualitative fragment ion of 123.1 m/z for at least one of $D_3$-THC and/or $D_3$-CBD and a predefined qualitative fragment ion of 308.2 m/z for D-COO-THC.

C23. The computer-program product of any of the previous or subsequent embodiments, wherein the THC and/or at least one THC metabolite and the CBD and/or at least one CBD metabolite exhibit different multiple reaction monitoring retention times.

C24. The computer-program product of any of the previous or subsequent embodiments, wherein a ratio of greater than 10 for CBD and/or at least one CBD metabolite as compared to THC and/or at least one THC metabolite indicates CBD use.

C25. The computer-program product of any of the previous or subsequent embodiments, wherein a ratio of less than 1.0 for CBD and/or at least one CBD metabolite as compared to THC and/or at least one THC metabolite indicates THC use.

C26. The computer-program product of any of the previous or subsequent embodiments, wherein the biological sample is urine.

C27. The computer-program product of any of the previous or subsequent embodiments, wherein the determining a ratio of the amount of the CBD and/or at least one CBD metabolite to the amount of the THC and/or at least one THC metabolite for the sample is performed on a computer.

C28. The computer-program product of any of the previous or subsequent embodiments, wherein the method distinguishes CBD use from THC use in a subject.

Additional Considerations

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium", "storage" or "memory" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to, portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

That which is claimed:

1. A method of identifying a subject as a CBD user or a THC user by measuring relative levels of at least one THC metabolite and at least one CBD metabolite in a urine sample obtained from a subject comprising the steps of:
    (a) performing tandem MS/MS on the urine sample to obtain MS/MS data comprising a predetermined MS/MS transition for the at least one THC metabolite and the at least one CBD metabolite, wherein the predetermined MS/MS transition comprises a transition for at least one predefined precursor ion of defined m/z and at least one quantitative fragment ion of a defined m/z for each of the at least one THC metabolite and the at least one CBD metabolite, and wherein the at least one THC metabolite comprises 11-carboxy Δ9-THC (COO-THC) and THC released from Δ9-THC glucuronide, and the at least one CBD metabolite comprises 7-carboxy-CBD (COO-CBD) and CBD released from CBD glucuronide;
    (b) determining an amount of the at least one THC metabolite and the at least one CBD metabolite in the urine sample based on the transitions in step (a); and
    (c) determining a ratio of the amount of the at least one CBD metabolite to the amount of the at least one THC metabolite for the urine sample, wherein the ratio indicates CBD use or THC use in the subject from whom the urine sample is obtained, thereby identifying the subject as either a CBD user or a THC user.

2. The method of claim 1, wherein the predetermined MS/MS transitions of step (a) further comprise at least one qualitative fragment ion of a defined m/z for each of the at least one THC metabolite and the least one CBD metabolite, and step (a) further comprises determining a transition for the at least one predefined precursor ion to the at least one qualitative fragment ion for the at least one THC metabolite and the at least one CBD metabolite.

3. The method of claim 2, wherein the transition for the at least one predefined precursor ion to the at least one qualitative fragment ion is used to confirm an identity of the at least one THC metabolite and the at least one CBD metabolite in the urine sample.

4. The method of claim 2, wherein the at least one quantitative fragment ion of defined m/z comprises at least one of: 123.1 m/z and/or 259.1 m/z and 135.1 m/z for THC released from Δ9-THC glucuronide; 123.1 m/z and/or 259.1 m/z and 135.1 m/z for CBD released from CBD glucuronide; 299.1 m/z and/or 187.1 m/z and 229.1 m/z for 11-carboxy Δ9-THC; and 299.1 m/z and/or 257.1 m/z and 229.1 m/z for 7-carboxy CBD.

5. The method of claim 1, wherein the at least one predefined precursor ion of defined m/z comprises at least one of: 315.1 m/z for THC released from Δ9-THC glucuronide; 315.1 m/z for CBD released from CBD glucuronide; 345.1 m/z for 11-carboxy Δ9-THC; or 345.1 m/z for 7-carboxy CBD.

6. The method of claim 1, wherein the at least one quantitative fragment ion of defined m/z comprises at least one of: 193.1 m/z for THC released from Δ9-THC glucuronide; 193.1 m/z for CBD released from CBD glucuronide; 193.1 m/z for 11-carboxy Δ9-THC; or 193.1 m/z for 7-carboxy CBD.

7. The method of claim 1, wherein performing tandem MS/MS of step (a) further comprises the use of a labeled isotope internal standard.

8. The method of claim 7, wherein the internal standard comprises at least one of D3-THC, D3-CBD, or D9-11-carboxy Δ9-THC.

9. The method of claim 1, wherein the at least one THC metabolite and the at least one CBD metabolite each exhibit different multiple reaction monitoring retention times.

10. The method of claim 1, wherein a ratio of greater than 10 for the ratio of the amount of the at least one CBD metabolite to the amount of the at least one THC metabolite indicates CBD use in the subject from whom the urine sample is obtained.

11. The method of claim 1, wherein a ratio of less than 1.0 for the ratio of the amount of the at least one CBD metabolite to the amount of the at least one THC metabolite indicates THC use in the subject from whom the urine sample is obtained.

12. A system to identify a subject as a CBD user or a THC user by measuring relative levels of at least one THC metabolite and at least one CBD metabolite in a urine sample comprising:
(a) a station for performing tandem MS/MS on the urine sample to obtain MS/MS data comprising a predetermined MS/MS transition for the at least one THC metabolite and the at least one CBD metabolite, wherein the predetermined MS/MS transition comprises a transition for at least one predefined precursor ion of defined m/z and at least one quantitative fragment ion of a defined m/z for each of the at least one THC metabolite and the at least one CBD metabolite, and wherein the at least one THC metabolite comprises 11-carboxy Δ9-THC (COO-THC) and THC released from Δ9-THC glucuronide, and the at least one CBD metabolite comprises 7-carboxy-CBD (COO-CBD) and CBD released from CBD glucuronide;
(b) a station for determining an amount of the at least one THC metabolite and the at least one CBD metabolite in the urine sample based on the transitions in step (a);
(c) a station for determining a ratio of the amount of the at least one CBD metabolite to the amount of the at least one THC metabolite for the urine sample; and
(d) a station for identifying the urine sample as being from a subject who has ingested THC and/or CBD and/or is indeterminate for ingesting either THC and/or CBD based on the ratio of the amount of the at least one CBD metabolite to the amount of the at least one THC metabolite for the urine sample.

13. The system of claim 12, wherein at least one station comprises one or more computers and a non-transitory computer readable storage medium containing instructions which, when executed on the one or more computers, cause the one or more computers to perform an action for the at least one station.

14. The system of claim 12, wherein a ratio of greater than 10 for the ratio of the amount of the at least one CBD metabolite to the amount of the at least one THC metabolite indicates CBD use in the subject from whom the urine sample is obtained, and/or wherein a ratio of less than 1.0 for the ratio of the amount of the at least one CBD metabolite to the amount of the at least one THC metabolite indicates THC use in the subject from whom the urine sample is obtained.

15. A computer-program product tangibly embodied in a non-transitory machine-readable storage medium, including instructions configured to cause one or more computers to perform actions to identify a subject as a CBD user or a THC user by measuring relative levels of at least one THC metabolite and at least one CBD metabolite in a urine sample comprising the following steps:
(a) performing tandem MS/MS on the urine sample to obtain MS/MS data comprising a predetermined MS/MS transition for the at least one THC metabolite and the at least one CBD metabolite, wherein the predetermined MS/MS transition comprises a transition for at least one predefined precursor ion of defined m/z and at least one quantitative fragment ion of a defined m/z for each of the at least one THC metabolite and the at least one CBD metabolite, and wherein the at least one THC metabolite comprises 11-carboxy Δ9-THC (COO-THC) and THC released from Δ9-THC glucuronide, and the at least one CBD metabolite comprises 7-carboxy-CBD (COO-CBD) and CBD released from CBD glucuronide;
(b) determining an amount of the at least one THC metabolite and the at least one CBD metabolite in the urine sample based on the transitions in step (a);
(c) determining a ratio of the amount of the at least one CBD metabolite to the amount of the at least one THC metabolite for the urine sample; and
(d) identifying the urine sample as being from a subject who has ingested THC and/or CBD and/or is indeterminate for ingesting either THC and/or CBD based on the ratio of the amount of the at least one CBD metabolite to the amount of the at least one THC metabolite for the urine sample.

16. The computer-program product of claim 15, wherein a ratio of greater than 10 for the ratio of the amount of the at least one CBD metabolite to the amount of the at least one THC metabolite indicates CBD use in the subject from whom the urine sample is obtained, and/or wherein a ratio of less than 1.0 for the ratio of the amount of the at least one CBD metabolite to the amount of the at least one THC metabolite indicates THC use in the subject from whom the urine sample is obtained.

* * * * *